(12) United States Patent
Koren et al.

(10) Patent No.: US 12,331,278 B2
(45) Date of Patent: Jun. 17, 2025

(54) CONTINUOUS MONITORING OF ALGAE CROPS USING MINIMUM OPTICAL INFORMATION

(71) Applicant: Yeda Research and Development Co. Ltd., Rehovot (IL)

(72) Inventors: Ilan Koren, Rehovot (IL); Assaf Vardi, Rehovot (IL); Yinon Rudich, Rehovot (IL); Adi Volpert, Rehovot (IL); Joseph Bolless, Rehovot (IL)

(73) Assignee: Yeda Research and Development Co. Ltd., Rehovot (IL)

( * ) Notice: Subject to any disclaimer, the term of this patent is extended or adjusted under 35 U.S.C. 154(b) by 947 days.

(21) Appl. No.: 17/474,208

(22) Filed: Sep. 14, 2021

(65) Prior Publication Data

US 2021/0403854 A1 Dec. 30, 2021

Related U.S. Application Data

(63) Continuation of application No. PCT/IL2020/050298, filed on Mar. 12, 2020.

(51) Int. Cl.
*C12M 1/34* (2006.01)
*C12Q 1/02* (2006.01)
(Continued)

(52) U.S. Cl.
CPC .............. *C12M 41/46* (2013.01); *C12Q 1/02* (2013.01); *G01N 21/31* (2013.01); *G01N 21/6486* (2013.01)

(58) Field of Classification Search
CPC ........ C12M 41/46; C12M 41/06; C12M 1/34; C12M 31/00; C12M 35/02; C12M 21/02;
(Continued)

(56) References Cited

U.S. PATENT DOCUMENTS

| 8,244,477 B1* | 8/2012 | Embaye ................ G01N 21/59 702/19 |
| 2005/0239044 A1 | 10/2005 | Seibert et al. |
| 2012/0077253 A1* | 3/2012 | Burkhead ................ C12N 1/12 435/257.1 |

FOREIGN PATENT DOCUMENTS

| CN | 101726742 | 6/2010 |
| CN | 104374758 | 2/2015 |

(Continued)

OTHER PUBLICATIONS

Nguyen-Ngoc, Hanh, Claude Durrieu, Canh Tran-Minh. "Synchronous-scan flurescence of algal cells for toxicity assessment of heavy metals and herbicides" Ecotoxicology and Environmental Safety. vol. 72, Issue 2, pp. 316-320. Feb. 2009. (Year: 2009).*

(Continued)

*Primary Examiner* — Michael L Hobbs

(57) ABSTRACT

A method for monitoring species of algae for stress comprises growing a test set of algae of a given species, applying a stress of a predetermined kind to some of the algae, and irradiating the algae at a predetermined first set of wavelengths. The algae are then monitored at a predetermined second set of wavelengths to detect fluorescence and/or absorbance carried out on the first set of wavelengths by the stressed algae. The detected fluorescence and/or absorbance is compared for each irradiation wavelength between the stressed algae and unstressed algae to find signs indicating the applied stress. There is then a stage of searching through combinations of respective irradiation wavelengths and detected wavelengths to find a minimal set of irradiating and (Continued)

detected wavelengths that detects the stress. The smallest size set is then used in irradiating further sets of algae of the tested species to detect the given stress.

24 Claims, 18 Drawing Sheets
(14 of 18 Drawing Sheet(s) Filed in Color)

(51) Int. Cl.
  *G01N 21/31* (2006.01)
  *G01N 21/64* (2006.01)
(58) Field of Classification Search
  CPC ...... C12Q 1/02; G01N 21/31; G01N 21/6486; G01N 2021/6419; G01N 2021/6421; G01N 2021/8466; G01N 2021/8883
  USPC .............................. 435/288.7, 292.1; 47/1.4
  See application file for complete search history.

(56) References Cited

FOREIGN PATENT DOCUMENTS

| CN | 104634771 | 5/2015 |
|---|---|---|
| GB | 2504981 | 2/2014 |
| JP | 2015-049227 | 3/2015 |
| WO | WO 2015/120144 | 8/2015 |
| WO | WO 2018/009967 | 1/2018 |
| WO | WO 2020/183474 | 9/2020 |

OTHER PUBLICATIONS

Communication Pursuant to Article 94(3) EPC Dated Nov. 3, 2023 From the European Patent Office Re. Application No. 20715476.6 (3 Pages).
Translation Dated Nov. 6, 2023 of Notice of Reason(s) for Rejection Dated Oct. 26, 2023 From the Japan Patent Office Re. Application No. 2021-550066. (5 pages).
Office Action Dated Jan. 9, 2024 From the Israel Patent Office Re. Application No. 286383. (4 Pages).
Notice of Reason(s) for Rejection Dated Apr. 10, 2024 From the Japan Patent Office Re. Application No. 2021-550066. (4 pages).
Translation Dated Apr. 22, 2024 of Notice of Reason(s) for Rejection Dated Apr. 10, 2024 From the Japan Patent Office Re. Application No. 2021-550066. (4 pages).
Takahashi et al. "Bioessay of Components Fluted from Electric Furnace Steel Slag Using Microalgae Chlorella", Tetsu-to-Hagane, 101(9): 42-50, 2015.
Notice of Reason(s) for Rejection Dated Oct. 26, 2023 From the Japan Patent Office Re. Application No. 2021-550066. (5 pages).
International Preliminary Report on Patentability Dated Jun. 16, 2021 From the International Preliminary Examining Authority Re. Application No. PCT/IL2020/050298. (19 Pages).
International Search Report and the Written Opinion Dated Aug. 17, 2020 From the International Searching Authority Re. Application No. PCT/IL2020/050298. (24 Pages).
Invitation to Pay Additional Fees Dated Mar. 9, 2021 From the International Preliminary Examining Authority Re. Application No. PCT/IL2020/050298. (5 Pages).
Invitation to Pay Additional Fees, Communication Relating to the Results of the Partial International Search and the Provisional Opinion Dated Jun. 4, 2020 From the International Searching Authority Re. Application No. PCT/IL2020/050298. (14 Pages).
Office Action and Search Report Dated Dec. 19, 2019 From the Israel Patent Office Re. Application No. 265385. (5 Pages).
Written Opinion Dated Apr. 26, 2021 From the International Preliminary Examining Authority Re. Application No. PCT/IL2020/050298. (9 Pages).
Kula et al. "Metabolic Activity, the Chemical Composition of Biomass and Photosynthetic Activity of Chlorella Vulgaris Under Different Light Spectra in Photobioreactors", Engineering in Life Sciences, XP055720672, 14(1): 57-67, Jan. 2014.
Matsui et al. "Spectrophotometry Can Monitor Changes in Algal Metabolism Triggered by Nutrient Deficiency in Nannochloropsis Oculata Cultured Under Various Light-Emitting Diode Light Regimes", Fisheeries Science, XP036669427, 85(1): 167-176, Puplished Online Oct. 9, 2018.
Mazzinghi "A Laser Diode Fluorometer for Field Measurements of the F685/F730 Chlorophyll Fluorescence Ratio", Review of Scientific Instruments, XP000635835, 67(10): 3737-3744, Oct. 1996.
Nguyen-Ngoc et al. "Synchronous-Scan Fluorescence of Algal Cells for Toxicity Assessment of Heavy Metals and Herbicides", Ecotoxicology and Environmental Safety, XP055697152, 72(2): 316-320, Feb. 2009.
Roemer et al. "Robust Fitting of Fluorescence Spectra for Pre-Symptomatic Wheat Leaf Rust Detection With Support Vector Machines", Computers and Electronics in Agriculture, XP028118215, 79(2): 180-188, Sep. 19, 2011.
Singh et al. "Machine Learning for High-Throughput Stress Phenotyping in Plants", Trends in Plant Science, XP029397427, 21(2): 110-124, Dec. 2015.
White et al. "PAM Fluorometry as a Tool Microalgal Nutrient Stress and Monitor Cellular Neutral Lipids", Bioresource Technology, 102(2): 1675-1682, Available Online Oct. 1, 2010.

* cited by examiner

Control 4h

| Excitation \ Emission | 440 | 460 | 480 | 500 | 520 | 540 | 560 | 580 | 600 | 620 | 640 | 660 | 680 | 700 | 720 | 740 | 760 | 780 | 800 | 820 | 840 |
|---|---|---|---|---|---|---|---|---|---|---|---|---|---|---|---|---|---|---|---|---|---|
| 440 | 241.3333 | 308.3333 | 323.3333 | 255.3333 | 198.6667 | 162.3333 | 113.6667 | 83.3333 | 60.3333 | 33.3333 |
| 460 | 0 | 249 | 266.6667 | 283 | 214 | 166.6667 | 123 | 97.6667 | 674.6667 | 3552 | 1466 | 663 | 335 | 123 | 69.66667 | 60.3333 | 48.33333 |
| 480 | 0 | 0 | 199 | 189.3333 | 194.6667 | 214 | 166.6667 | 123 | 786.6667 | 4081.333 | 1722 | 880.6667 | 787.3333 | 143.6667 | 89 | 61 | 30.66667 |
| 500 | 0 | 0 | 0 | 93.3333 | 172.6667 | 107.3333 | 82.3333 | 538 | 2866 | 1221.667 | 580.6667 | 569.3333 | 294.6667 | 102.6667 | 63.6667 | 48.3333 | 26.66667 |
| 520 | 0 | 0 | 0 | 0 | 95 | 99.66667 | 86.66667 | 57.3333 | 368.6667 | 1917 | 865.333 | 448.6667 | 381 | 211 | 77.33333 | 45.33333 | 29 | 22.33333 |
| 540 | 0 | 0 | 0 | 0 | 0 | 76 | 102 | 73.3333 | 68.66667 | 71.3333 | 396.3333 | 1802.667 | 776.6667 | 431 | 390 | 194.6667 | 74 | 48 | 35.3333 | 35 |
| 560 | 0 | 0 | 0 | 0 | 0 | 0 | 0 | 122 | 90 | 67.33333 | 72.3333 | 407 | 1880.333 | 817.1333 | 428 | 223.6667 | 81.66667 | 55.66667 | 24 | 12.66667 | 16 |
| 580 | 0 | 0 | 0 | 0 | 0 | 0 | 0 | 0 | 73.66667 | 43.33333 | 39.33333 | 122.6667 | 570.6667 | 278.6667 | 142.6667 | 121.3333 | 74.66667 | 28.66667 | 26.3333 | 24.66667 |
| 600 | 0 | 0 | 0 | 0 | 0 | 0 | 0 | 0 | 0 | 28.33333 | 27 | 63.33333 | 292.6667 | 157 | 87 | 75 | 40 | 20 | 21.33333 | 6.33333 | 22.33333 |
| 620 | 0 | 0 | 0 | 0 | 0 | 0 | 0 | 0 | 0 | 0 | 13 | 55.66667 | 235.6667 | 121 | 64.66667 | 57.66667 | 35.66667 | 13.33333 | 7 | 3 | 1 |
| 640 | 0 | 0 | 0 | 0 | 0 | 0 | 0 | 0 | 0 | 0 | 0 | 46.33333 | 220.6667 | 212 | 102.3333 | 56.66667 | 54.33333 | 30 | 15 | 3 | 1 |
| 660 | 0 | 0 | 0 | 0 | 0 | 0 | 0 | 0 | 0 | 0 | 0 | 0 | 0 | 116 | 52 | 46 | 31 | 20 | 18 | 19 | 18 |
| 680 | 0 | 0 | 0 | 0 | 0 | 0 | 0 | 0 | 0 | 0 | 0 | 0 | 0 | 179.6667 | 101.3333 | 81.33333 | 53.66667 | 27 | 14 | 14 | 23.66667 |
| 700 | 0 | 0 | 0 | 0 | 0 | 0 | 0 | 0 | 0 | 0 | 0 | 0 | 0 | 0 | 116.3333 | 107 | 59.33333 | 27 | 18 | 17.33333 | 18.66667 |
| 720 | 0 | 0 | 0 | 0 | 0 | 0 | 0 | 0 | 0 | 0 | 0 | 0 | 0 | 0 | 0 | 13 | 10 | 8.666667 | 9 | 13 | 25 |
| 740 | 0 | 0 | 0 | 0 | 0 | 0 | 0 | 0 | 0 | 0 | 0 | 0 | 0 | 0 | 0 | 0 | 1 | 2.33333 | 3 | 1.66667 | 7 |
| 760 | 0 | 0 | 0 | 0 | 0 | 0 | 0 | 0 | 0 | 0 | 0 | 0 | 0 | 0 | 0 | 0 | 0 | 3.66667 | 0.33333 | 5.66667 | 20.66667 |
| 780 | 0 | 0 | 0 | 0 | 0 | 0 | 0 | 0 | 0 | 0 | 0 | 0 | 0 | 0 | 0 | 0 | 0 | 0 | 11 | 17 | 19.33333 |
| 800 | 0 | 0 | 0 | 0 | 0 | 0 | 0 | 0 | 0 | 0 | 0 | 0 | 0 | 0 | 0 | 0 | 0 | 0 | 0 | 14.33333 | 19.33333 |
| 820 | 0 | 0 | 0 | 0 | 0 | 0 | 0 | 0 | 0 | 0 | 0 | 0 | 0 | 0 | 0 | 0 | 0 | 0 | 0 | 0 | 0 |

FIG. 7

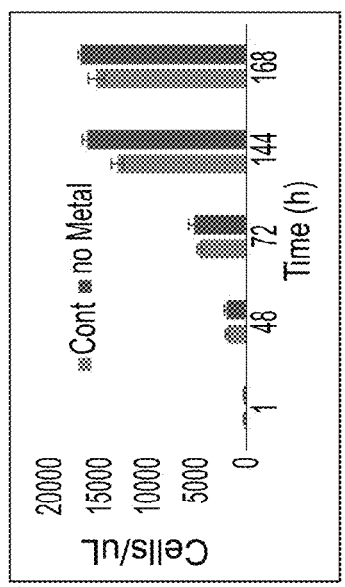
FIG. 12A
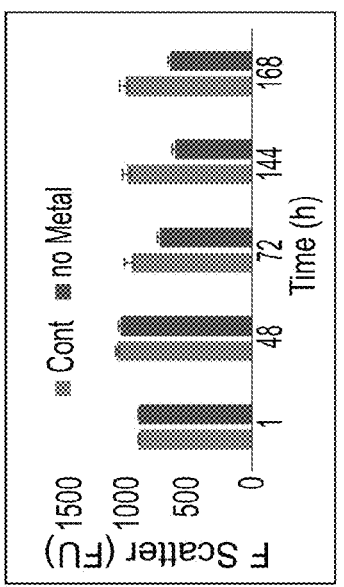
FIG. 12C
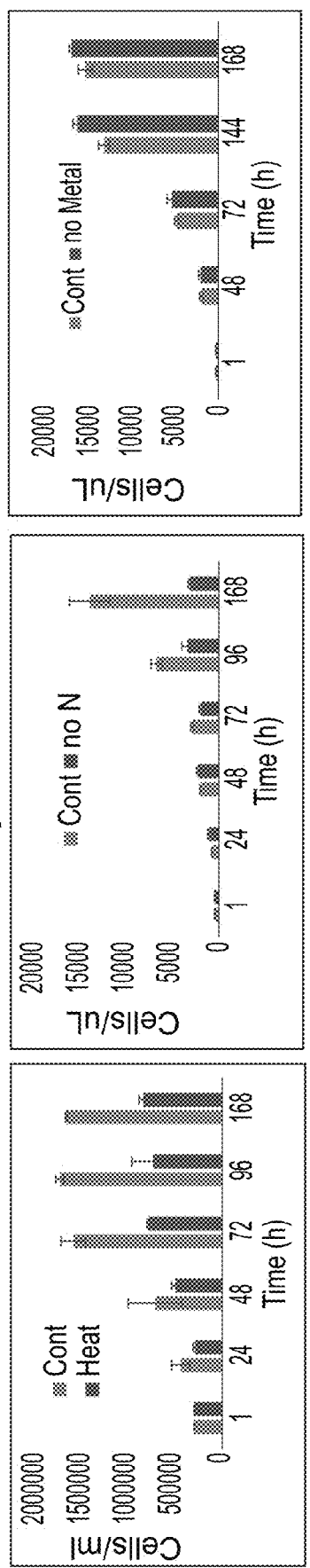
FIG. 12E
FIG. 12B
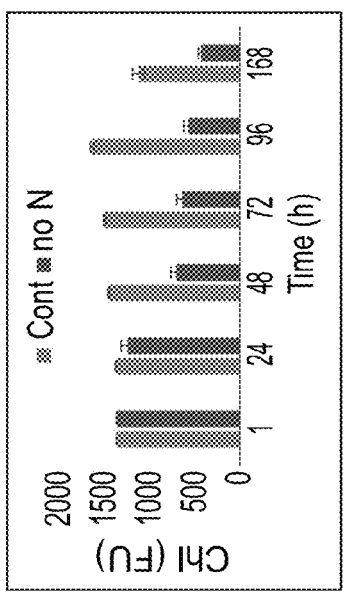
FIG. 12D
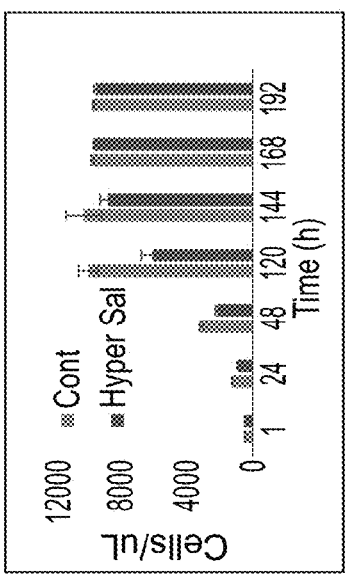
FIG. 12F

*N.salina*

*C.desicatta*

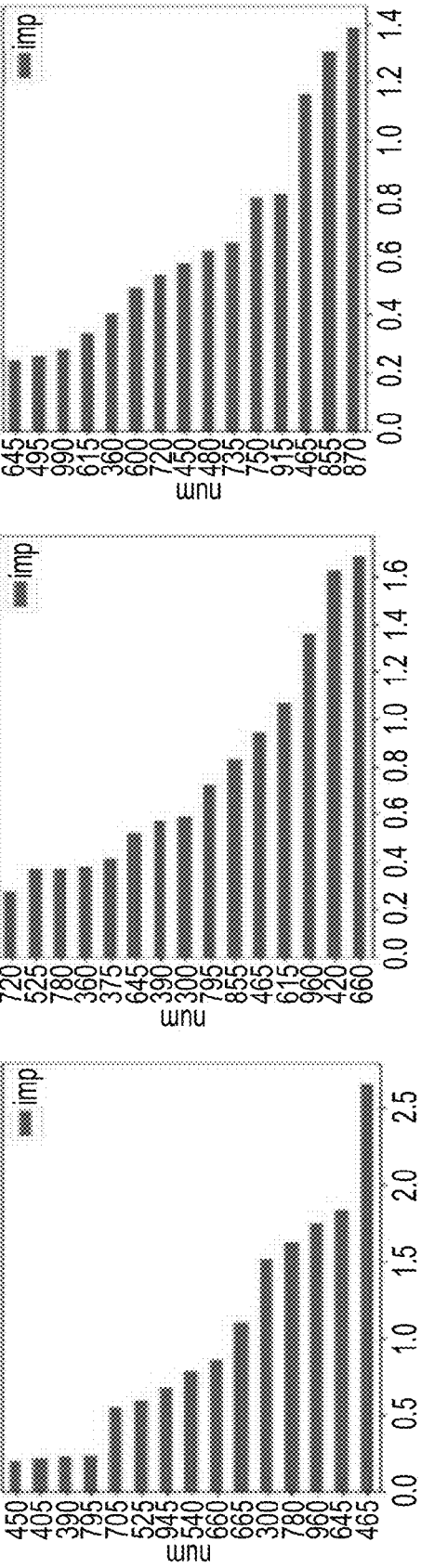
FIG. 15A – FIG. 15F. Absorbance all data specific classification (*P. tricornutum*)

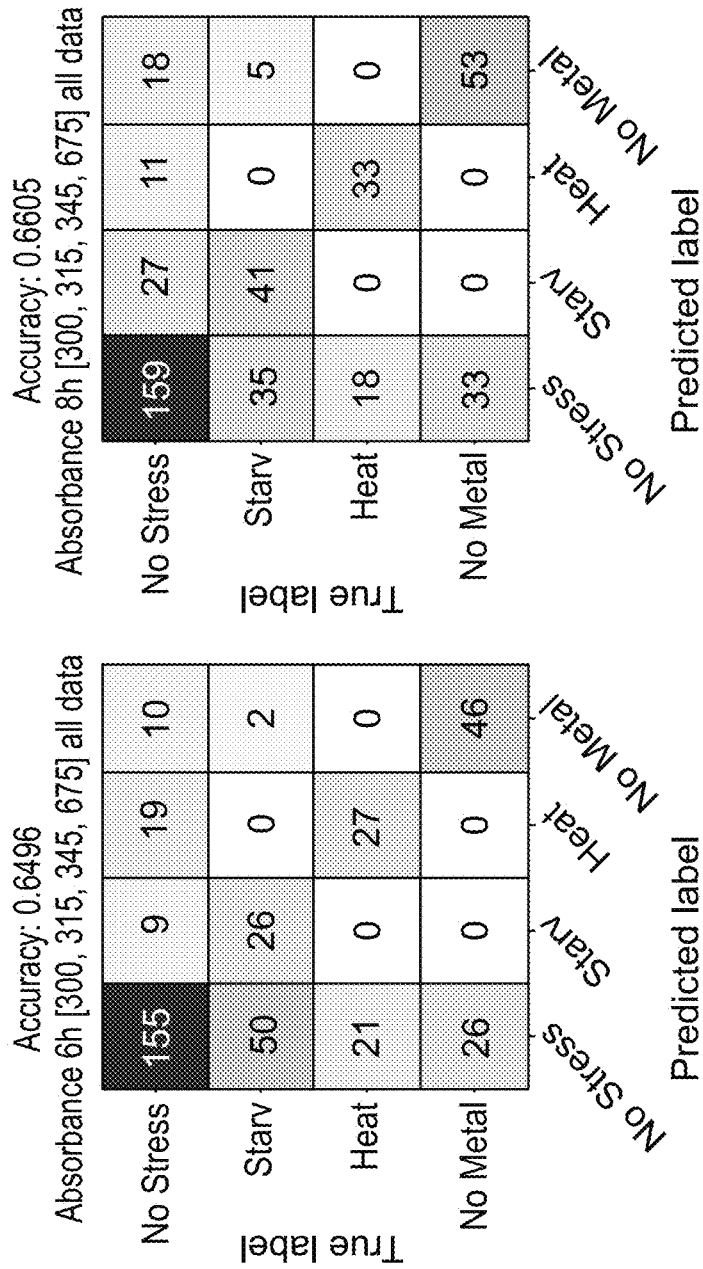

CONTINUOUS MONITORING OF ALGAE CROPS USING MINIMUM OPTICAL INFORMATION

RELATED APPLICATIONS

This application is a Continuation of PCT Patent Application No. PCT/IL2020/050298 having International filing date of Mar. 12, 2020, which claims the benefit of priority of Israel Patent Application No. 265385 filed on Mar. 14, 2019. The contents of the above applications are all incorporated by reference as if fully set forth herein in their entirety.

FIELD AND BACKGROUND OF THE INVENTION

The present invention, in some embodiments thereof, relates to a method and apparatus for continuous monitoring of algae crops and, more particularly, but not exclusively, to a method of monitoring that uses minimal optical information.

Microalgae may be considered one of the most promising feedstocks for sustainable production of commodities including human and animal nutrition supplements, cosmetics, pharmaceuticals, $CO_2$ capture, bioenergy production and products for enabling nutrient removal from wastewater. Microalgae do not need to be grown on arable land, can be grown on seawater on residual nutrients, have a high areal productivity, are rich in oils, proteins and carbo-hydrates and the algal biomass can be fractionated into both food and non-food products. Certain species of microalgae are even candidates for the production of biofuels due to their high productivity and high oil content. Currently most of the microalgae biomass production is being done in systems which are variations of the basic common systems: open raceway ponds (ORP), horizontal tubular photo bioreactors (PBR), stacked horizontal tubular PBR and flat panels (FP-PBR).

Successful farming of microalgae presents some challenges, a desired amount of biomass has to be produced at a controlled quality level, while facing hazards and various potential stresses such as bacterial or viral contamination, potential grazers, nutrient depletion and other non-optimal environmental conditions such as light regime and temperature changes. Microalgae farmers often encounter some of these hazards dealing with stressed or contaminated culture when it is too late to respond and recover the batch, ending up with a collapse of the culture.

Optimizing growth despite all the mentioned hazards and maintaining high quality and productivity is a key factor necessary for successful and profitable farming of microalgae. Today microalgae growers monitor their algae cultures offline, required to take their samples to a laboratory for analysis, which is typically carried out once a day using basic lab tools and expensive labor.

There is today no known way of carrying out online biological monitoring with high resolution of time, meaning allowing collection of data several times a day, perhaps even hourly, yet such monitoring can benefit the grower considerably in multiple aspects, by early detection of stress in time to save crops, optimizing growth cycles and use of resources (nutrients, electricity, labor, etc.) and accurate management of the production process.

SUMMARY OF THE INVENTION

The present embodiments may provide in situ monitoring of the algae using a per species calculated minimal set of wavelengths of light for fluorescence. Monitoring may indicate the microalgae wellbeing and may identify either early stress formation or general physiological state. The set of wavelengths is defined separately per microalgae species. The set may for example consist of one or more light sources (in different wavelengths) for excitation, and in addition one or more detectors for different wavelengths for fluorescent emission. In addition, detectors located on the opposite side of the sample from the excitation source may be used to detect absorption.

The embodiments further extend to a method of identifying the minimum set for any new algal species and stress.

According to an aspect of some embodiments of the present invention there is provided a method for monitoring species of algae for stress comprising:

growing a test set of algae of a first species;

applying a stress of a predetermined kind to some of the algae;

irradiating the algae at a predetermined first set of wavelengths;

monitoring the algae at a predetermined second set of wavelengths to detect fluorescence and/or absorbance of the stressed algae;

comparing detected fluorescence and/or absorbance for each irradiation wavelength between the stressed algae and unstressed algae to find signs indicating the applied stress;

searching through combinations of respective irradiation wavelengths and detected wavelengths to find a minimal set of irradiating and detected wavelengths that detects the stress; and using the smallest size set, irradiating further sets of algae of the first species to detect stress of the predetermined kind.

In an embodiment, the first set of wavelengths and the second set of wavelengths are built into optical matrices G(t) of detections at respective wavelength combinations, respective matrices containing results for different times.

An embodiment may comprise constructing variance (V) images collected per stress at the different times and generating a normalized G(NG) matrix, a relative dispersion (εG) matrix, a global ranked matrix (RG) and a line-ranked matrix (LG).

In an embodiment, the searching through combinations is carried out by applying machine learning to the matrices.

In an embodiment, the machine learning comprises using a combination of random decision forests and support vector machines.

In an embodiment, the machine learning comprises using convolutional neural networks.

In an embodiment, the stress of a predetermined kind is nitrogen stress.

In an embodiment, the second set of wavelengths comprises a range including 480 and 840 nm.

In an embodiment, the first set of wavelengths comprises a range including 440 nm and 800 nm.

In an embodiment, the range is covered in jumps of 20 nm.

In an embodiment, the irradiation is carried out using pulses.

In an embodiment, the first species is from the *Chlorella* genus.

In an embodiment, the smallest size set comprises less than five irradiating wavelengths and less than ten detection wavelengths.

In an embodiment, the smallest size set comprises less than three irradiating wavelengths and less than six detection wavelengths.

In an embodiment, the smallest size set comprises one irradiating wavelength and two detection wavelengths.

In an embodiment, the detecting stress using the minimal set comprises detecting a scatter in amplitudes in a first wavelength of the detection wavelengths compared to a second wavelength of the detection wavelengths An aspect of the present invention may relate to use of a minimal set of wavelengths obtained as above, to monitor algae being grown.

In an aspect, the invention may relate to algae grown using monitoring as above.

According to a further aspect of embodiments of the present invention there is provided a method of monitoring growth of algae for stress, comprising:

irradiating the algae at successive time intervals with at least one irradiation wavelength;

measuring fluorescence and/or absorbance from the algae at at least two detection wavelengths, the at least two detection wavelengths being different from the at least one irradiation wavelength;

comparing amplitudes of the at least two detection wavelengths, and determining presence of stress.

The method may comprise:

selecting a first stress factor for testing; and selecting a corresponding set of at least one irradiation wavelength and at least two detection wavelengths.

In an embodiment, the determining presence of stress comprises detecting a scatter in amplitudes in a first of the detection wavelengths compared to a second of the detection wavelength.

In a further aspect of embodiments of the present invention there is provided apparatus for monitoring algal growth for stress, comprising:

an irradiation source positionable to irradiate growing algae using at least one irradiation wavelength;

a detector positionable to detect fluorescence and/or absorbance from the growing algae, the detector configured to detect amplitudes, following the irradiation, at a plurality of detection wavelengths, the plurality of detection wavelengths being different from the at least one irradiation wavelength;

a comparator, configured to compare the amplitudes of the plurality of wavelengths and to determine from the comparison whether the growing algae is subject to a given stress.

In an embodiment, the at least one irradiation wavelength and the plurality of detection wavelengths are selected according to a species of the growing algae and for multiple stress types acting on the species.

In a further aspect of embodiments of the present invention there is provided apparatus for monitoring algal growth for stress, comprising:

an irradiation source positionable to irradiate growing algae using at least one irradiation wavelength;

a detector positionable to detect fluorescence and/or absorbance from the growing algae, the detector configured to detect amplitudes, following the irradiation, at a plurality of detection wavelengths, the plurality of detection wavelengths being different from the at least one irradiation wavelength; and a communication link configured to send detection results to a comparator, the comparator to compare the amplitudes of the plurality of wavelengths and to determine from the comparison whether the growing algae is subject to a given stress.

In a yet further aspect of embodiments of the present invention there is provided apparatus for remote monitoring algal growth for stress, comprising:

an input for obtaining detection results of a detector positioned to detect fluorescence and/or absorbance from growing algae, the detector configured to detect amplitudes, following irradiation at an irradiation wavelength, the detection being at a plurality of detection wavelengths, the plurality of detection wavelengths being different from the at least one irradiation wavelength;

a comparator, connected to the input, and configured to compare the amplitudes of the plurality of wavelengths and to determine from the comparison whether the growing algae is subject to a given stress.

Unless otherwise defined, all technical and/or scientific terms used herein have the same meaning as commonly understood by one of ordinary skill in the art to which the invention pertains. Although methods and materials similar or equivalent to those described herein can be used in the practice or testing of embodiments of the invention, exemplary methods and/or materials are described below. In case of conflict, the patent specification, including definitions, will control. In addition, the materials, methods, and examples are illustrative only and are not intended to be necessarily limiting.

Implementation of the method and/or system of embodiments of the invention can involve performing or completing selected tasks manually, automatically, or a combination thereof. Moreover, according to actual instrumentation and equipment of embodiments of the method and/or system of the invention, several selected tasks could be implemented by hardware, by software or by firmware or by a combination thereof using an operating system.

For example, hardware for performing selected tasks according to embodiments of the invention could be implemented as a chip or a circuit. As software, selected tasks according to embodiments of the invention could be implemented as a plurality of software instructions being executed by a computer using any suitable operating system. In an exemplary embodiment of the invention, one or more tasks according to exemplary embodiments of method and/or system as described herein are performed by a data processor, such as a computing platform for executing a plurality of instructions. Optionally, the data processor includes a volatile memory for storing instructions and/or data and/or a non-volatile storage, for example, a magnetic hard-disk and/or removable media, for storing instructions and/or data. Optionally, a network connection is provided as well.

BRIEF DESCRIPTION OF THE SEVERAL VIEWS OF THE DRAWING(S)

The patent or application file contains at least one drawing executed in color. Copies of this patent or patent application publication with color drawing(s) will be provided by the Office upon request and payment of the necessary fee.

Some embodiments of the invention are herein described, by way of example only, with reference to the accompanying drawings. With specific reference now to the drawings in detail, it is stressed that the particulars shown are by way of example and for purposes of illustrative discussion of embodiments of the invention. In this regard, the description taken with the drawings makes apparent to those skilled in the art how embodiments of the invention may be practiced.

In the drawings:

FIG. 7 is an example of the raw data measured in the learning component for 3 biological replicates of *Chlorella desiccata* at specific time points either under nitrogen starvation stress or optimal (control) conditions according to the present embodiments;

FIGS. 12A-12F are the results of heat, nitrogen and metal stress tests on *P. tricornutum*;

Figures 14A, 14B:
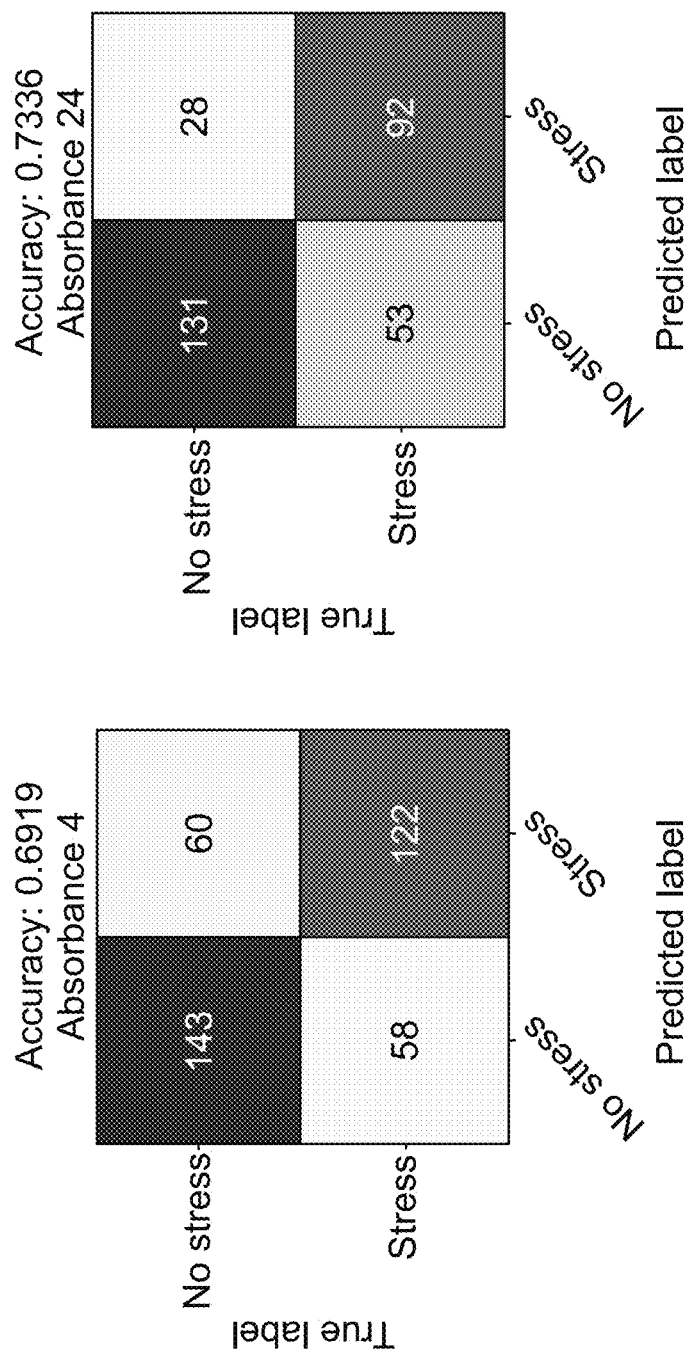
Figure 14C:
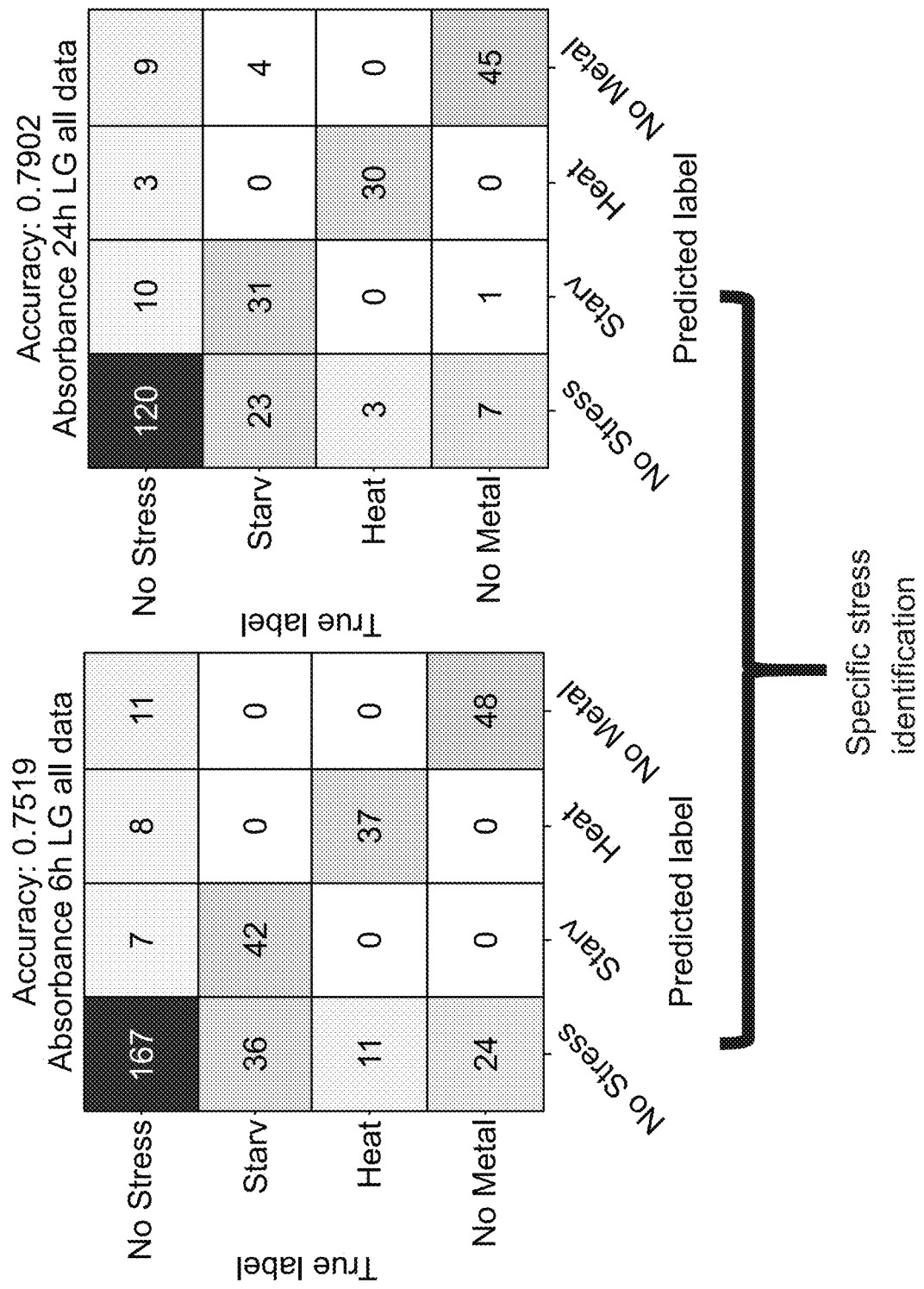
Figures 16A, 16B, 16C:
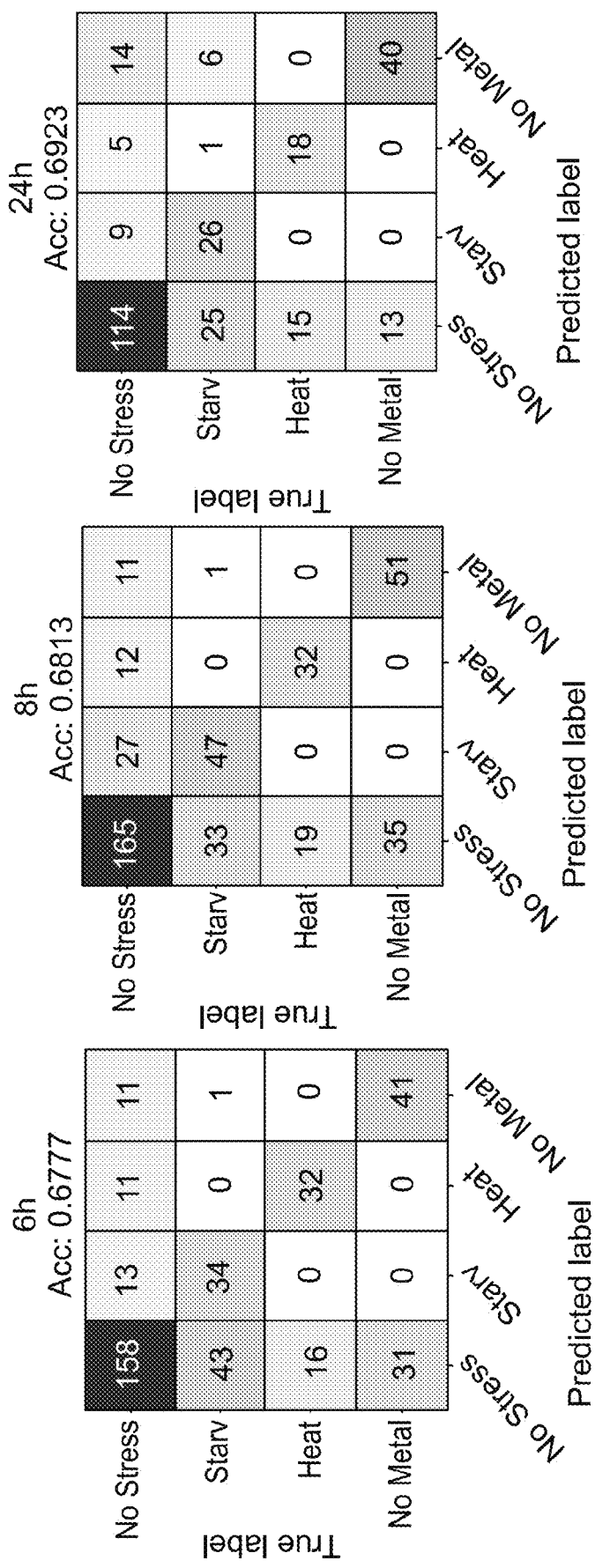

FIGS. 14A-C show binary classifications of the *P. tricornutum* algae into stressed and non-stressed populations 4 hours and 24 hours post stress initiation respectively;

FIGS. 15A-15F show absorbance and all-data classification for *P. tricornutum* in accordance with embodiments of the present invention;

FIGS. 16A-C illustrate specific stress classifications for *P. tricornutum* based on absorbance in only 10 wavelengths in accordance with the present invention; and FIGS. 17A and 17B show specific stress classifications for *P. tricornutum* based on absorption in only five wavelengths, at six hours and eight hours post stress respectively, according to embodiments of the present invention.

DESCRIPTION OF SPECIFIC EMBODIMENTS OF THE INVENTION

As explained, the present invention, in some embodiments thereof, relates to a method and apparatus for continuous monitoring of algae crops which may be carried out on-line and in situ, and, more particularly, but not exclusively, to a method that makes use of minimal optical information.

As discussed in the background, biological monitoring of the microalgae in the current art is carried out offline. Online in-situ monitoring may be provided in the present embodiments and may track the environmental and physiological dynamics of the microalgae, allowing the grower better and more accurate management of the production process. For example online and/or in-situ monitoring may allow optimal use of resources such as growing facilities, nutrients, electricity, culture condition optimization and would provide a possibility to get an early detection of stress while the grower can still respond and save the culture.

The monitoring approach of the present embodiments may rely on the specific passive and active optical properties of the cultivated microalgae. The embodiments may take into consideration:

1) Different algae strains contain different pigment compositions and display different optical properties.
2) Under physiological perturbations of the microalgae, there are changes in the optical properties of the algae culture, whether fluorescence or absorbance, some of which will be expressed at early stages. Indeed, patterns and clusters in the absorption-excitation-fluorescence matrix (AEF) and its derivatives are specific to the I) algae type, II) stress type and amplitude, III) time from stress initiation.

Monitoring the optical parameters of the algae, using new ways of representing the data and new methods for image classification may thus provide an innovative technology for in-situ monitoring of the alga physiological state and may provide early stress-specific identification.

The present embodiments may enable continuous optical monitoring of microalgae and their physiological state using light sources and detectors for fluorescence in few wavelengths combinations that are species-specific. The present embodiments may minimize the required essential optical data for monitoring the algae physiological state and optimize growth, that is they may find a minimal number of excitation light sources for detectors which in combination allow for early detection of a stress situation. The system then monitors the algae using only that minimal set of parameters. The minimal set may be specific to the species of algae being monitored, as discussed. The system is composed of two units: central and peripheral. The central unit is composed of two components: learning, which is essentially carried out once per species per stress type, and monitoring, which is carried out continuously, using the minimal sets of fluorescence signal sources and detectors as optimized in the learning stage. The learning component is typically a laboratory-based unit that monitors the growth dynamics of a specific algae type a) during optimal growth conditions (the control) and b) under specific a-biotic and biotic stress conditions. At each time step, the system measures fluorescence response using a discrete array of well-defined excitation sources, measuring the spectral fluorescence emissions. The present embodiments may use relatively weak fluorescence information to compose an image-like matrix of optical responses that serves as input for deep-learning image analysis and classification methods.

Early signs of different stresses have varying patterns and clustering properties in an optical-fluorescence matrix. The present embodiments may use the matrix, its variance and a few further matrices derived from nonlinear manipulations of initial matrices, as will be described in greater detail below, to detect early response to a specific stress type. The data collected in the matrices may then provide the input to a deep learning system aimed at minimizing the essential spectral information.

The second peripheral unit is a light, small, weather proof modular unit that contains the minimal (essential) spectral sources and detectors. Such units may be installed at the algae growth site and may transfer optical measurements continuously to the interpreting component in the central unit. The real-time spectral interpretation may be based on the network optimization gained in the training state of the first unit.

Before explaining at least one embodiment of the invention in detail, it is to be understood that the invention is not necessarily limited in its application to the details of construction and the arrangement of the components and/or methods set forth in the following description and/or illustrated in the drawings and/or the Examples. The invention is capable of other embodiments or of being practiced or carried out in various ways.

The present embodiments may provide a system that monitors the microalgae physiological state and provides early warnings of stress, using continuous optimal measurements. Using artificial intelligence, a method according to the present embodiments may minimize the required optical data that is needed for monitoring the algae physiology and growth and provide early signs of stress.

Figure 1:
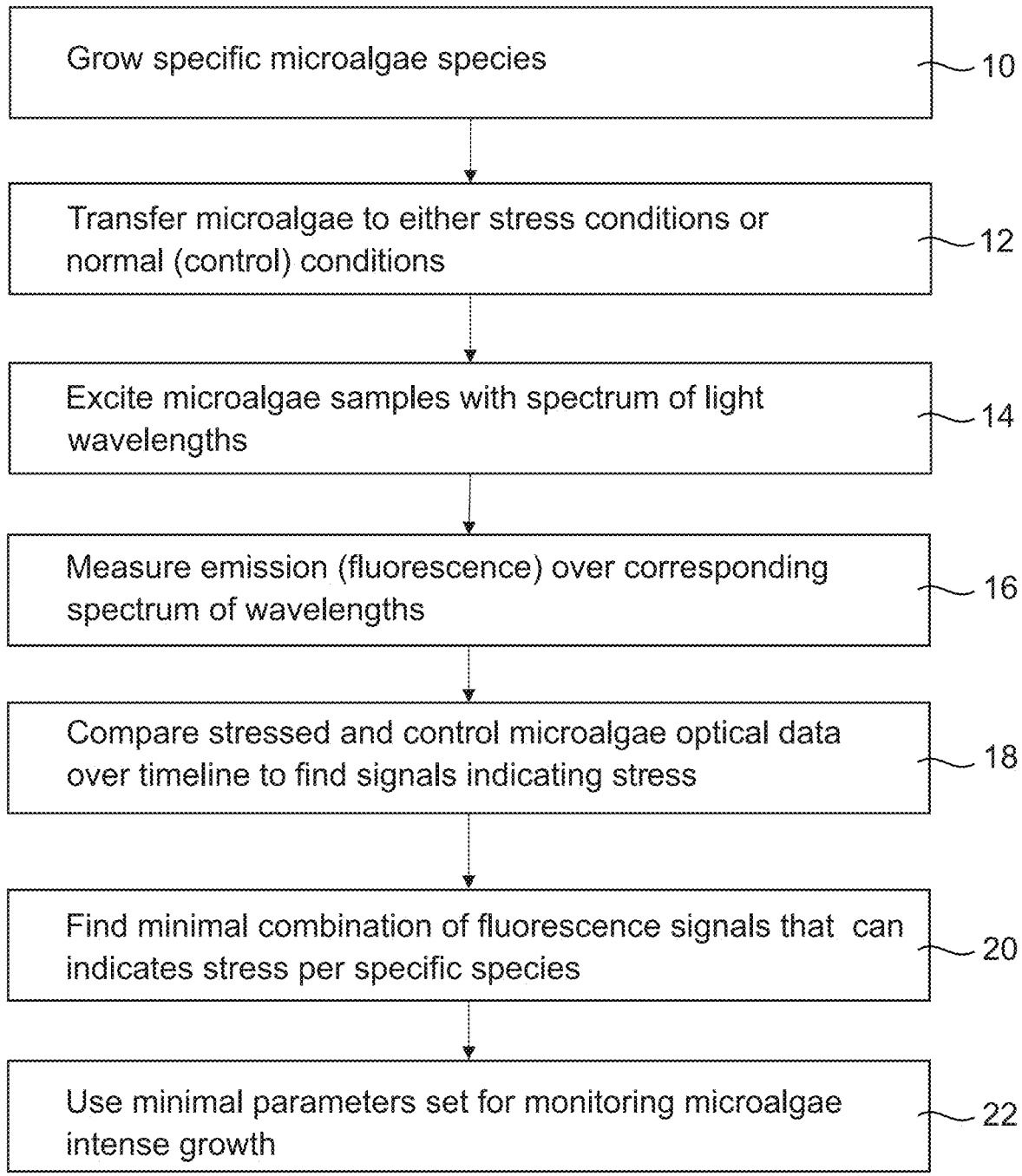
FIG. 1 is a simplified flow chart illustrating a process according to the present invention of finding a minimal set of irradiation and monitoring wavelengths, or other optical parameters for monitoring algal growth.

Reference is now made to FIG. 1, which is a simplified flow chart illustrating a process according to the present embodiments of finding a minimal set of irradiation and monitoring wavelengths (optical parameters) for monitoring microalgae growth. The method initially comprises growing a test set of microalgae of a particular species 10. A stress of a predetermined kind, say lack of an essential nutrient, or some kind of contamination is applied to some of the algae being grown with the rest kept as a control 12.

In box 14, the growing algae are excited with a spectrum of light wavelengths, for example the set of wavelengths in the vertical axis of FIG. 7.

In box 16, the microalgae are monitored for emission over a corresponding set of wavelengths, for example those along the horizontal axis in FIG. 7. At each wavelength, the amplitude of fluorescence following excitation at a given irradiation wavelength is detected and a matrix is filled in. Figures are obtained for both the stressed algae and the control.

In box 18, the detected amplitudes for each irradiation wavelength between the stressed microalgae and control microalgae are compared, and wavelength combinations giving differences between the stress and control subjects may be used as indications of the applied stress.

In box 20 a process is carried out of searching through the various combinations of respective irradiation wavelengths and detected fluorescence wavelengths to find a smallest size set of irradiating and detected wavelengths that reliably detects the applied stress. The idea is to produce a large matrix of combinations, and then find from that matrix a very small number of combinations that best detect the stress. For example something like a 20×20 matrix may be the starting point and 2×2 matrix may be the finishing point, depending on such variables as the specific stress applied and the species of alga being grown.

In box 22, once the smallest size set of irradiating and monitoring wavelengths has been found, then that set is now used for routine real time in situ monitoring of algal growth.

Figure 2:
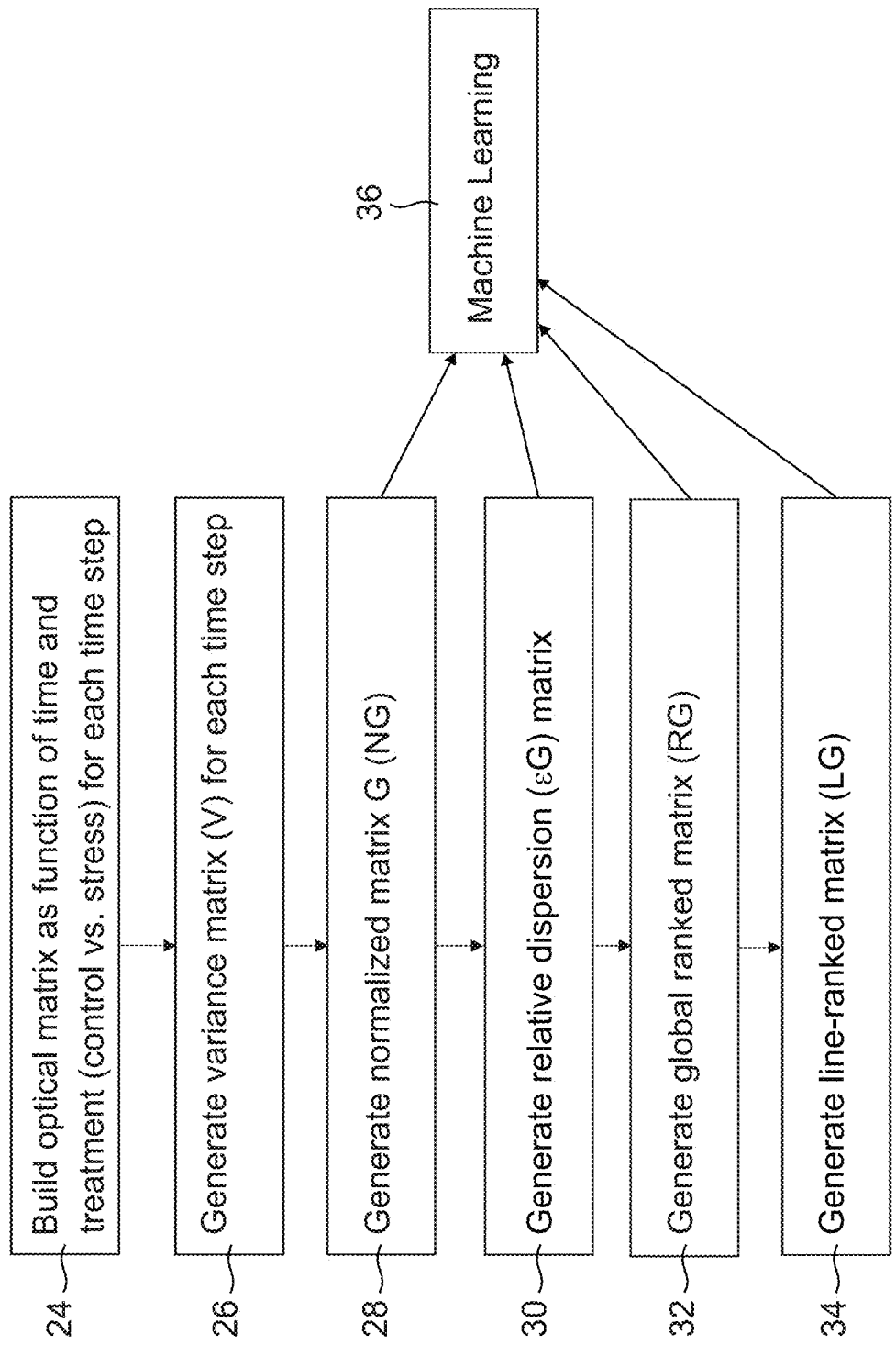
FIG. 2 is a simplified flow chart showing in greater detail part of the process of FIG. 1.

Reference is now made to FIG. 2, which illustrates one way in which machine learning may be carried out. In box 24, the two sets of wavelengths and corresponding detected amplitudes are built into optical matrices G(t) of detections. The matrix is set up as a function of time, by entering monitoring results over successive times.

In box 26, for the various different times, variance (V) matrices are collected. From the variance matrix a normalized G (NG) matrix is set up in box 28. A relative dispersion (εG) matrix is set up in box 30. A global ranked matrix (RG) is set up in box 32 and a line-ranked matrix (LG) is set up in box 34.

The various derived matrices are then applied as inputs to machine learning in box 36. Searching through combinations may then be carried out by applying machine learning to the matrices. The machine learning may be supervised machine learning and may be told which results are stress and which results are not. The process then finds out what is the minimal set of inputs from the matrices that will reliably distinguish between stressed and non-stressed samples.

In other embodiments, combinatorial analysis, or direct inspection of the matrix can be used.

In embodiments, the machine learning of box 36 uses a combination of random decision forests and support vector machines, as will be discussed below. Alternatively the machine learning may use convolutional neural networks.

One form of stress that may be applied is lack of nitrogen, in which the stressed sample is not supplied with nitrogen, starting at some point in its growth.

The monitoring equipment may initially monitor the growing algae over a range of wavelengths that includes 480 and 840 nm, say in regular jumps, for example jumps of 20 nm.

The irradiation wavelengths used to set up the matrix may comprise a range including 440 nm and 800 nm. Again these may be in regular jumps, say of 20 nm.

Irradiation may be carried out using pulses.

The algae may for example be a species from the *Chlorella* genus.

The machine learning may determine the minimal number of wavelengths required, both for sources and detectors for a robust, statistically significant early stage stress detection. A smallest size set that reliably identifies stress may differ between different species of algae and may cover different applied stresses. In the example herein, a minimum sized set was one excitation wavelength and two emission wavelengths, but other examples may be of different sizes. For example there may be five, three, or one excitation wavelengths, with ten, six or two detection wavelengths. Certain detection wavelengths may accompany specific excitation wavelengths. Some excitation wavelengths may be associated with multiple detection wavelengths and some with just a single detection wavelength. Again, some excitation wavelengths may be associated with more detection wavelengths than other excitation wavelengths.

Figure 10A:
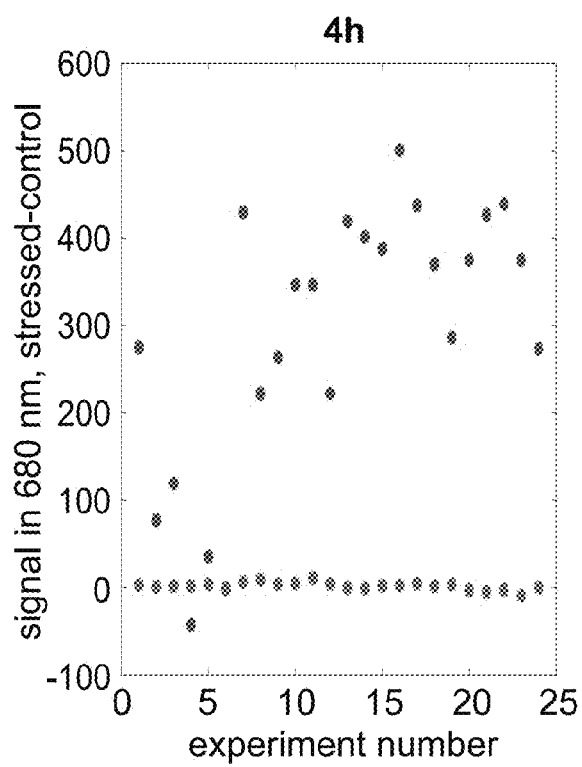
FIGS. 10A and 10B are results at two different fluorescence signals (excitation of 440 nm and emission of 480 nm or 680 nm) at 4 hours and 48 hours respectively after application of a stress to the growing *Chlorella desiccata* sample of FIGS. 8 and 9.
Figure 10B:
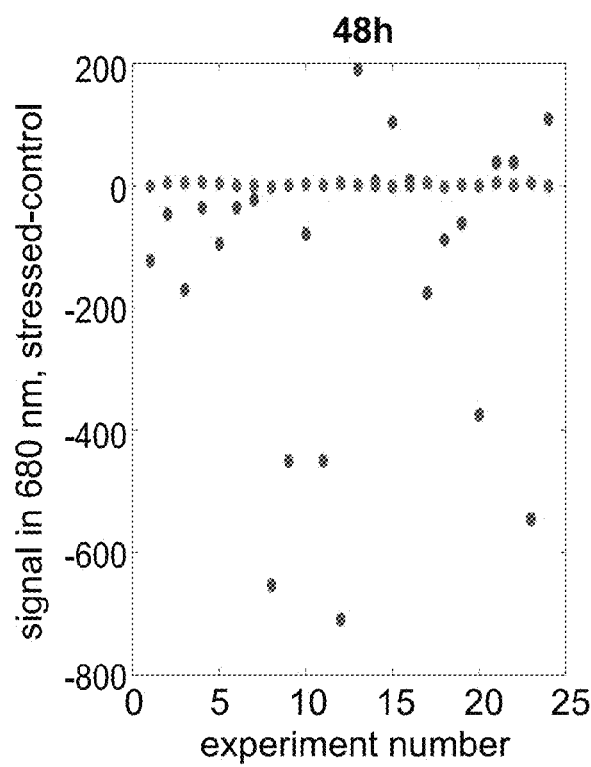

As illustrated in FIGS. 10A and 10B, and discussed in further detail below, detecting stress using the smallest size set may involve detecting a scatter in amplitudes in one of the detection wavelengths compared to a second wavelength which may be used as a reference or baseline. Thus the smallest size set of wavelengths obtained as described above, may be used to monitor algae being grown, for example commercially. As shown in FIG. 10A, the impact of stress is clear at just four hours after the stress is applied, and the grower is thus alerted to any problems much sooner than currently possible. Furthermore, the monitoring can be much more widely applied to the growing algae.

Figure 3:
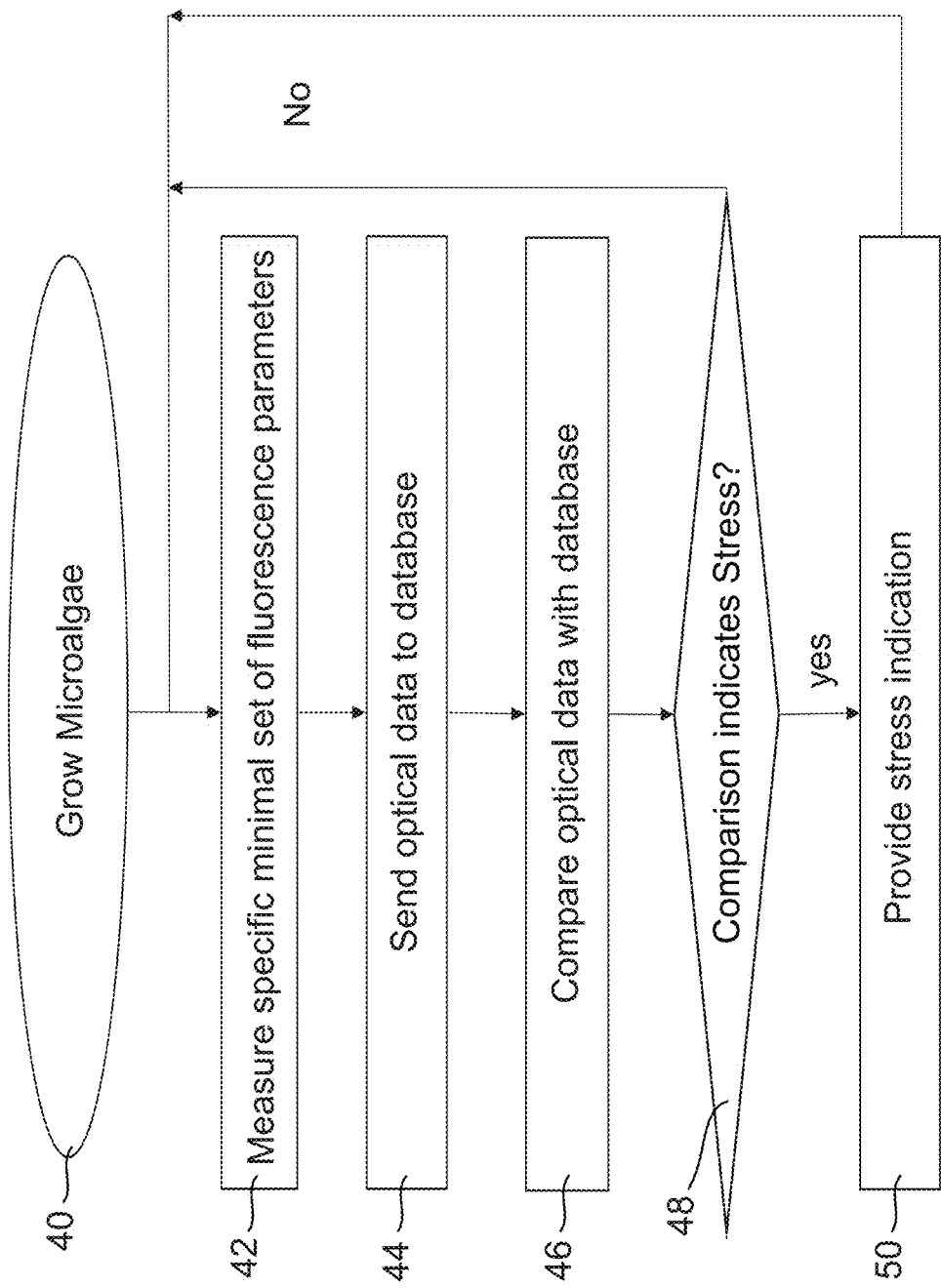
FIG. 3 is a simplified flow chart showing how to monitor growing microalgae using only the minimal set of parameters found in FIG. 1.

Reference is now made to FIG. 3, which is a simplified flow chart showing how to monitor growing microalgae using only the minimal set of parameters found in FIG. 1 according to the present embodiments.

Microalgae is grown—box 40 and monitoring is applied in box 42 by irradiating the algae at successive time intervals with the irradiation wavelength or wavelengths recommended for the given species and stress type. Fluorescence and/or absorbance is then measured in box 44 at detection wavelengths that go with the irradiation wavelength and the algal species and stress type. The number of monitored wavelengths per irradiation wavelengths may be one or more and at least one monitoring wavelength may be different from the irradiation wavelength. It is noted that, in the case of fluorescence, all of the detector wavelengths are longer than the source. In the case of absorption measurements the detector is generally at the same wavelength as the source.

In box 46, amplitudes of the detection wavelengths are compared to find out if there is a pattern indicating stress. If there is an indication of stress—box 48—then an alarm is issued so that the grower can take necessary action. In either case monitoring continues.

Figure 4:
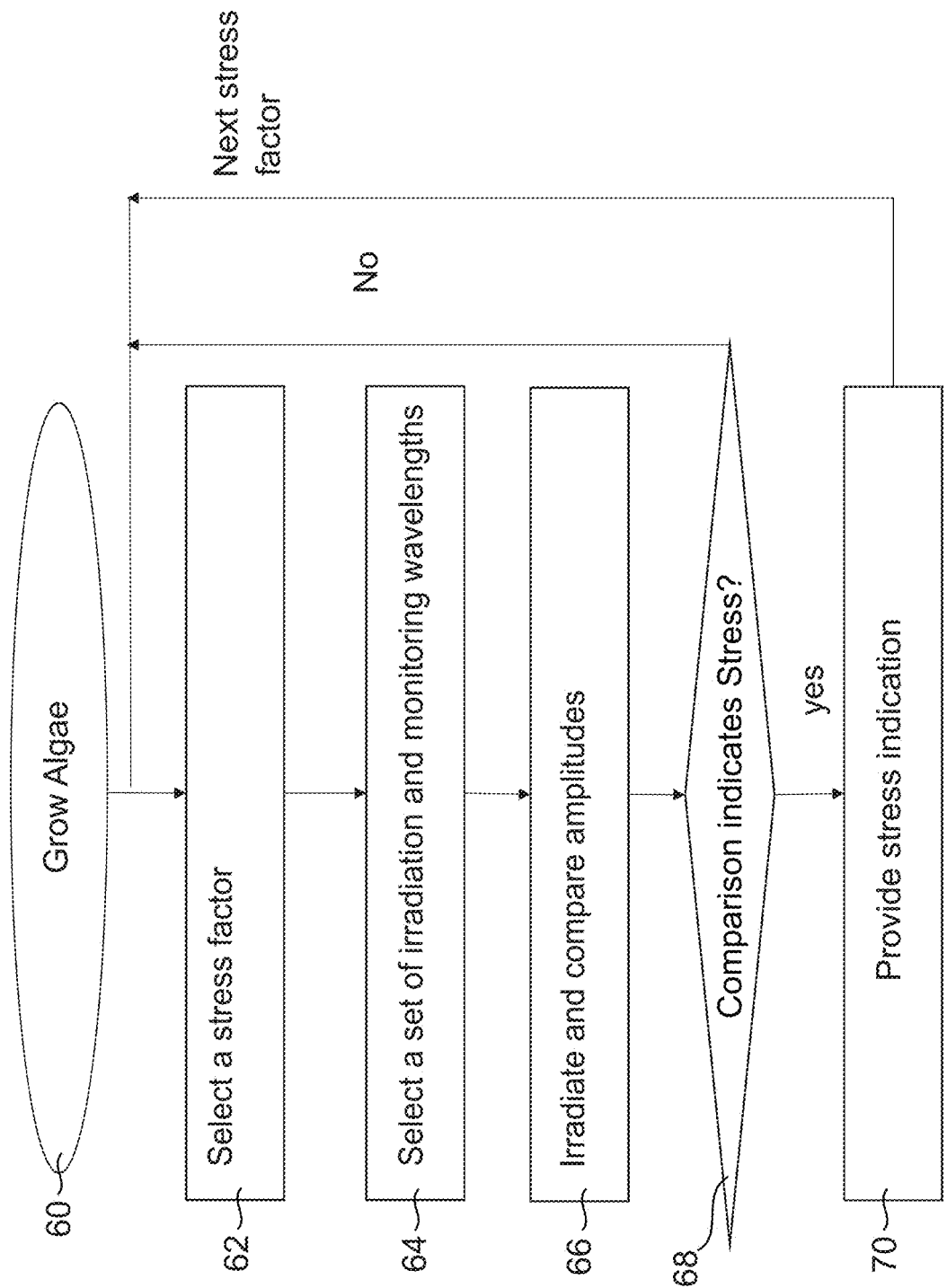
FIG. 4 is a simplified flow chart showing a process for monitoring different stresses according to embodiments of the present invention.

Reference is now made to FIG. 4, which is a simplified flow chart showing how the method of FIG. 3 may be carried out for multiple stress factors on algae being grown in 60. In box 62 a first stress factor is selected and then a corresponding set of test wavelengths is chosen in box 64. Irradiation and monitoring is carried out as before 66 and if the comparison indicates stress than a notification is issued 70. Afterwards the stress factor may be changed and a different set of test wavelengths may be used.

Figure 5:
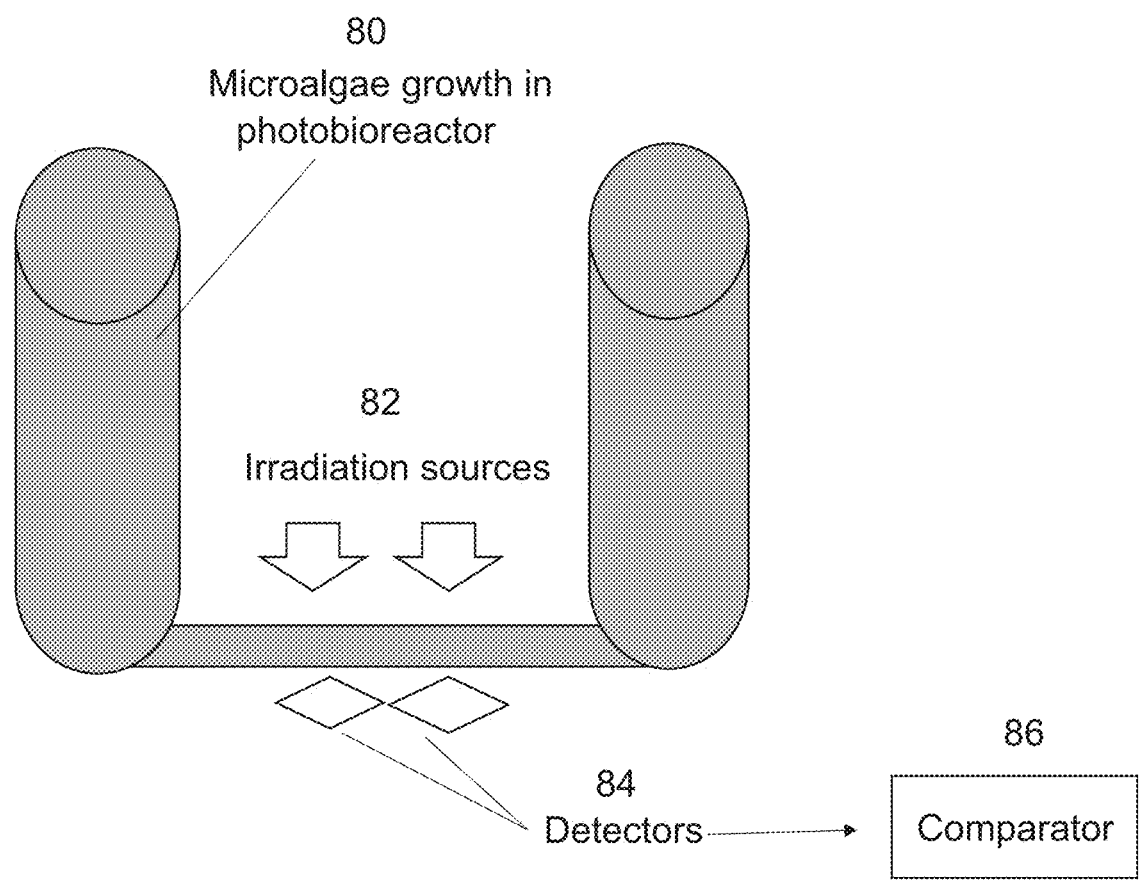
FIG. 5 is a simplified schematic block diagram of apparatus for monitoring algal growth according to embodiments of the present invention.

Reference is now made to FIG. 5 which is a simplified block diagram illustrating monitoring apparatus for monitoring microalga growth for stress according to the present embodiments. FIG. 5 shows algal growth 80, which may be in a pool, pond or photobioreactor or any other kind of microalgae growth unit. The algae may be grown commercially. An irradiation source 82 is positioned to irradiate the growing algae 80 using one or more selected irradiation wavelengths. The irradiation wavelengths may for example be selected using the minimization process discussed herein.

Detectors 84 are positioned to detect fluorescence and/or absorbance, produced as a result of the irradiation, from the growing algae 80. Fluorescence signals are expected to be detected only at longer wavelengths compared to the source. Absorbance is generally measured at the same wavelength. Comparator 86 compares amplitudes of the various detected wavelengths to determine whether the growing algae is subject to a given stress. As discussed in respect of FIG. 4, the apparatus may test for multiple stresses, and different wavelength combinations may be selected for each of the different stresses.

In addition, the same apparatus may be used for different species of algae, and different irradiation and detection wavelengths may be selected according to the current species and the current stress of interest.

The system according to the present embodiments is composed of two main units: a central and a peripheral unit. The central unit has two functioning components: the learning and the signal interpretation components. The system continuously learns and improves algae monitoring efficiency and increases the levels of detail, say adding new algae and additional stress types. The optical signal interpretation element may collect the spectral information from peripheral units, may process the information and provide information on the algae wellbeing and early warning for various stress types.

The peripheral units may be composed of light, small, weather proof and relatively cheap optical measuring devices (OMD) that contain the minimal (essential) spectral sources and detectors. The OMDs are designed to be modular, such that the optical specifications may be easily modified to provide the best spectral settings per microalgae species and growing conditions. Several peripheral units may be installed at the algae growth sites and may collect optical signals that may continuously or intermittently be transmitted to the central unit. The interpretation and, when needed the real-time, early warning signals may be provided by the central unit.

Figure 6:
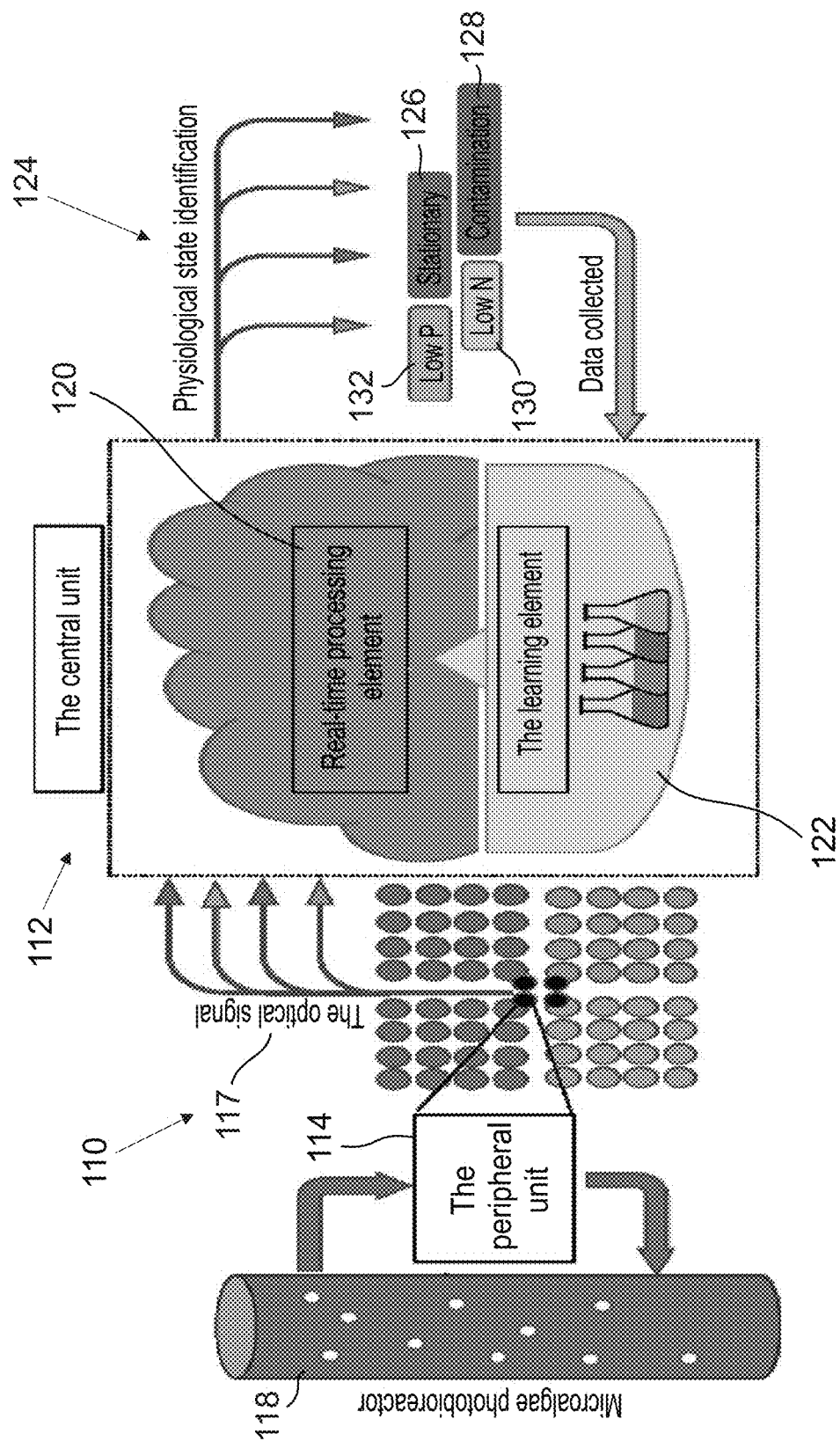
FIG. 6 is a simplified block diagram of all the microalgae monitoring components using the minimal set of optical parameters found in FIG. 1.

Reference is now made to FIG. 6, which is a simplified block diagram schematically illustrating components of a continuous monitoring system according to embodiments of the present invention. System 110 comprises central 112 and peripheral 114 units. The central unit 112 contains the biological and optical instruments that allow growing of cultures under optimal and stressed conditions and measure their detailed optical responses in time relative to stress initiation, this part forming the learning element 122 discussed herein below. The peripheral unit is composed of simple optical measuring devices (OMD) that contain the minimal essential spectral sources and detectors, which minimal set is obtained as discussed herein. The OMD optical signal 117 is continuously transferred from the microalgae growth unit, for example microalgae photobioreactor 118, to processing element 120 in the central unit in which the signal is analyzed and the central unit then continuously investigates the algae's physiological state. This provides the users real time evaluations of the culture's well-being and early warnings of stresses.

The learning/training component 122 in the central unit contains the biological and optical instruments, discussed in greater detail herein below, that allow growing of cultures under optimal conditions, to provide a control, and further samples grown under key typical stresses and stress conditions. In each case the optical responses are measured in real time. At each time step, the system measures spectral absorption, scattering and fluorescence response using continuous array of monochromatic sources as well as sources with a wide spectral range.

The central unit may output a result indicating the identified physiological state of the algae. Output 124 may indicate that the sample is healthy 126, or various kinds of stress, for example contamination 128, low nitrogen 130, or low phosphate 132.

It will be appreciated that the learning/training component may be dispensed with by end users who merely want to monitor their algal growth based on already available results.

For the learning stage, the system uses a weak fluorescence response measured over several channels to infer a robust signature for early stress stages. For each algae species, each stress condition is applied, and following the stress initiation, the system produces an image-like absorption-excitation-fluorescence matrix (AEF matrix denoted here as G(t)) that is composed of fluorescence and absorption responses to all excitation sources. At each stage the optical measurements are repeated 3 times, carried out at a preset interval and allowing for mean and variance calculations per each time step.

The present embodiments may show that different stress types trigger different fluorescence and absorption signatures, creating different patterns and clusters in G(t). The optical matrix G(t) as well its variance (V) images collected per stress at different time steps are transformed to several related matrixes such as a normalized G (NG) matrix, a relative dispersion (εG) matrix, a global ranked matrix (RG) and a line-ranked matrix (LG). These image matrixes serve as the input to a deep learning system that classifies the data into stress type and stage and provides the minimum essential spectral information for stress detection, as will be explained.

Model System

In order to demonstrate the effect of a stress on the optical changes we use *Chlorella desiccata* (CDX) as a model microalgae from the *Chlorella* genus which is widely used in the industry. We select a mild nitrogen limitation, namely f/2 media diluted X5 to fresh media, and where the nitrogen component is omitted to produce the stressed samples. Lack of nitrogen is selected as a key stress, due to its known effect on optical changes and to the common occurrence of nitrogen starvation in microalgae lipid production.

Microalgae Culture and Growth

Microalgae cultures are grown in artificial seawater (ASW) supplemented with f/2 media, and the stressed samples are left without nitrogen. The samples are kept at 24° C. with 16:8 h light:dark cycles. 150 μmol photon·m-2·sec-1 light was supplied by cool-white LED lights between 7:00 and 23:00. In all the experiments conducted n=3.

Measuring Instrument

We use a microplate reader (Tecan infinite pro200) to measure both the absorbance and the fluorescence scan of the microalgae cultures. We use three biological replicas of both the control and the stressed samples; each is 200 μL by volume and all set in a flat transparent 96 well plate.

Results

On the extraction of an Absorption-Excitation-Fluorescence (AEF) matrix and its derivatives:

The quality of the optical measurements depends heavily on the spectral bandwidth and accuracy of excitation sources. Therefore, we provide a tailor-made light source and spectral measurement probe that is composed by well-specified light source and narrow filtering methods to produce isolated and spectrally narrow excitation sources upon request. Per each discrete emission of the narrow sources, continuous spectral measurements are taken and the readouts may form individual lines in the G matrix.

The source may generate narrow bandwidth pulses in a wide spectral range. We aim for each pulse to have about 2 nm width, ranging from 200 to 3000 nm.

Per each excitation pulse (f) centered around a wavelength ($\varphi$) i.e. $f\_\varphi$, the weak fluorescence signal (g) may be measured for all wavelengths ($\lambda$) larger than $\varphi$ i.e. $g\_\lambda$ such that $\lambda > \varphi$.

The output luminescence of such measurements may be arranged in a triangular matrix (G) as shown in FIG. 7, for which the y-axis is y and each line represents the luminescence yield in longer wavelengths $g\_\lambda$. The first line of G will be the spectral absorption measurements. More particularly, FIG. 7 shows an example of the averaged measured Absorption-Excitation-Fluorescence (AEF) matrix. The Y-axis shows the excitation wavelength and the X-axis rows shows the fluorescence response in all wavelengths larger than the source. Per Each Absorption-Excitation-Fluorescence measurement n=3 (biological replicates) are provided per each sample in each time step.

Figure 8:
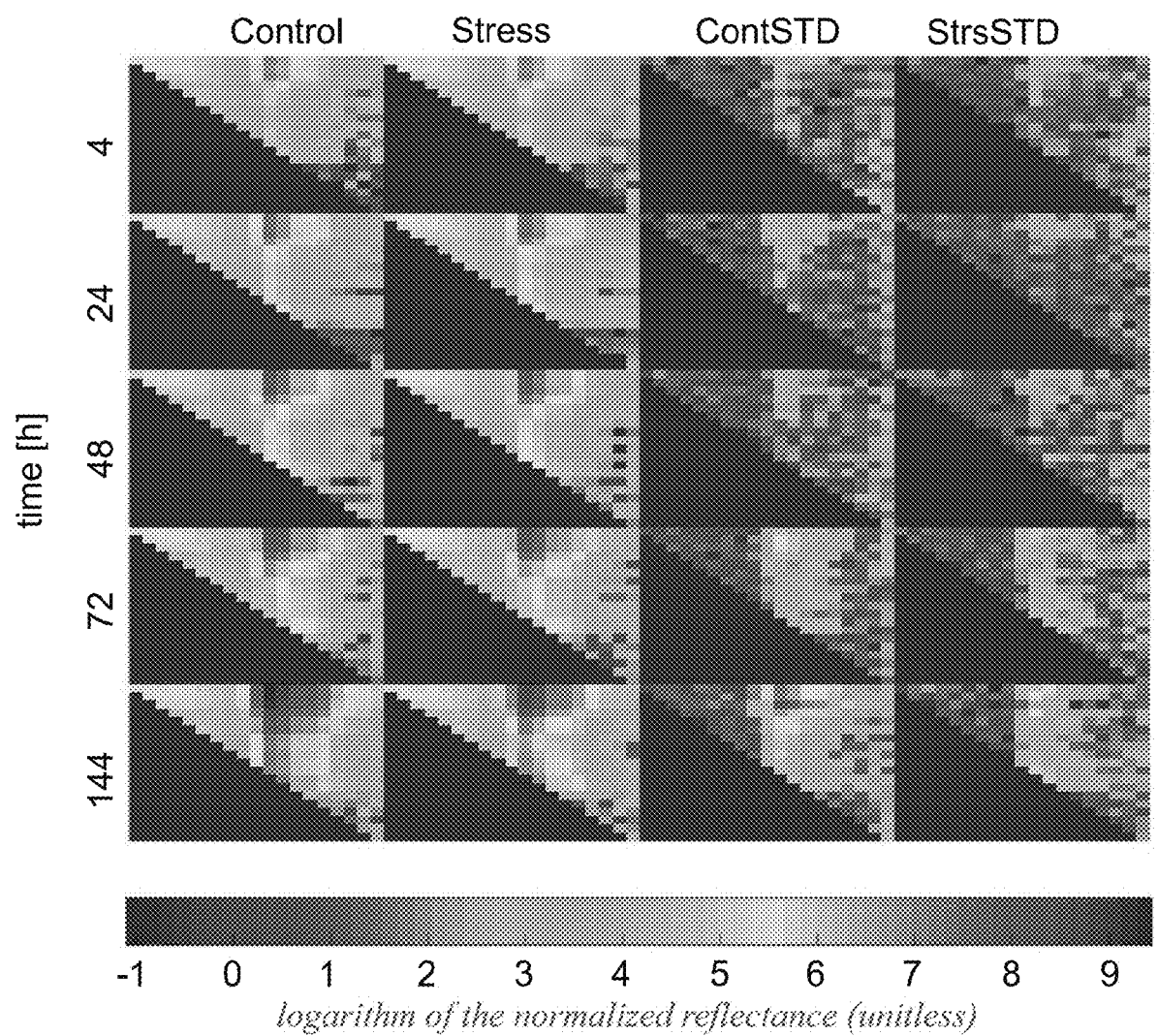
FIG. 8 is an example of the raw data (including standard deviations) measured and visualizes in the learning component for 3 biological replicates of *Chlorella desiccata* at multiple time points either under nitrogen starvation stress or optimal (control) conditions according to the present embodiments.

Reference is now made to FIG. 8, which shows an example of the raw data (including standard deviations) measured and provides a visualization in the learning component for 3 biological replicates of *Chlorella desiccata* at multiple time points either under nitrogen starvation stress or optimal (control) conditions according to the present embodiments. The $1^{st}$ column on the left is the control data, the $2^{nd}$ is for a stressed set, the $3^{rd}$ and $4^{th}$ are the standard deviations of the 3 replicates for the control ($3^{rd}$) and the stressed ($4^{th}$). Each line refers to measurement time from the initiation of the stress (4 h 24 h 48 h 72 h and 144*h*). The colors indicate the logarithm of the normalized reflectance (unit less).

Figure 9:
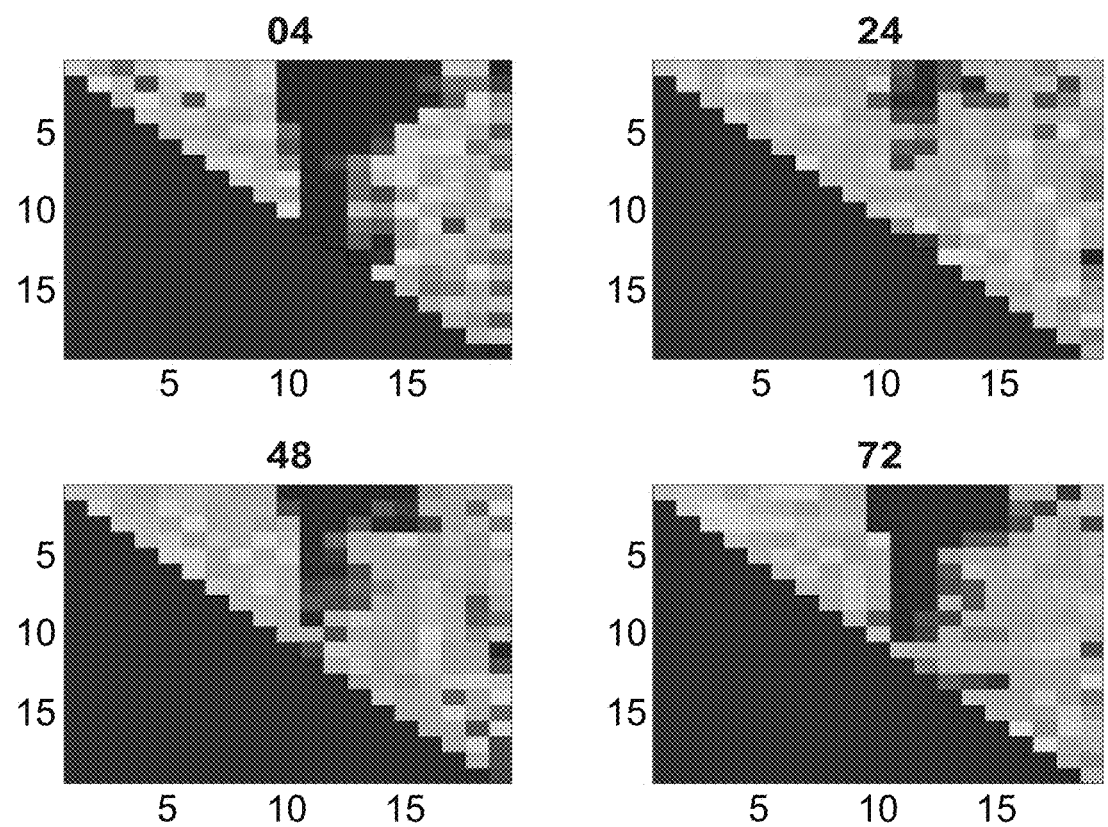
FIG. 9 is an example of early detection of stress for *Chlorella desiccata* with N starvation stress, for the set shown in FIG. 8, in which each matrix shows normalized differences between the control and the stressed set as a function of time after stress initiation (4 h 24 h 48 h 72 h), according to the present embodiments.

Reference is now made to FIG. 9, which illustrates an example of early detection of stress for CDX with nitrogen starvation stress, for the set shown in FIG. 8, according to the present embodiments. Each matrix shows normalized differences between the control and the stressed set as a function of time after stress initiation (4 h 24 h 48 h 72 h). It shows non-monotonic response of the central wavelengths group. During the period of 4 to 24 hours there is a relative increase in the fluorescence response of the central group followed by a sharp decrease. Such a non-trivial response as an initial increase in the signal can serve as an early warning of stress, providing a clear indication in ~12 h as compared to standard stress-detection methods that detect such stress in more than ~72 h (see the signal in FIG. 8).

Machine Learning Approach

The present embodiments may employ Machine Learning (ML) approaches to distill the minimal signal required for finding robust mathematical relationships between the algae stress, and the optical readouts as a function of the time from applying stress. We carry out the machine learning and data minimization for two culture-growth modes as follows:

1) Following the growth dynamics from the initial stage of dilute culture through the exponential stage and the saturated stage; and 2) In a chemostat mode for which the culture is in a steady state for which there is a balance between the sink (dilution) and growth.

ML is usually classified into supervised learning and unsupervised learning. In the present embodiments, we use mostly concepts from the supervised branch of ML. Specifically, we use advanced regression approaches, Random Forest (RF) decision trees and Support Vector Machines (SVM) as the main method. In parallel, we employing approaches based on Deep Learning (DL).

In the learning stage, two sets are measured simultaneously: control (unperturbed culture) and stressed. Per each set, 5 matrixes are measured and calculated:

1) G, the averaged Absorption-Excitation-Fluorescence of $g\_\lambda$ for all sources $f\_\varphi$ of the measured luminescence (Gc for the control and Gs for the stressed).
2) Vc and Vs the standard deviation matrixes
3) εGc and εGd the relative dispersion matrixes
4) Rc and Rs the global ranking matrixes for which each pixel is replaced by its ordered rank index.
5) Lc and Ls line (or column) ranking matrixes for which each pixel is replaced by its ordered rank index per line (or column).

The input per each time in the above 10 images (5 matrixes for the stressed and 5 for the control) reflect the state of the culture at a given time since the initiation of stress as compared to the reference. In order to extract the minimal spectral information required for a robust detection of stress, per each algae type and per each stress type, the present embodiments may selectively reduce the information content. Once the system is trained to robustly detect stress in early stages using all data we analyze patterns in the input matrix as the main indicators. The training is repeated but with more limited information, that is to say fewer channels and fewer detectors, with the aim of distilling the more repeatable and therefore more robust signals marking the stress. To do so we use an analysis method which gradually decreases the information content of the matrices.

As an example, for such an approach we may detect CDX with nitrogen starvation stress after 4 hours by using one light source of 440 nm and two detectors, one at 480 nm and one in 680 nm. The stressed culture enhances the fluorescence signal at 680 nm in the first few hours and only later reduces it. This allows us to indicate signs of stress by comparing two fluorescence signals, one that is not affected (480 nm) and one that is affected (680 nm). We note that the typical time for detection of such stress in the current art is 3 days.

Results are shown in FIGS. 10A and 10B. The minimal signal approach involves detecting CDX with nitrogen starvation stress at a time of 4 hours using one source of 440 nm and two detectors at 480 nm and 680 nm. Blue dots mark 680 differences (stressed-control) and the red dots mark the 480 differences (stressed-control). At 4 hours (left panel) the 680 signal of the stressed cultures is increasing as compare to the control whereas at 48 h (right panel) the stressed 680 signal decreases.

Applications

Continuous monitoring of the algae may optimize production costs and increase the growers total yield through the following:
1) Preventing collapse due to algal mortality events by allowing the growers to respond to stresses in real time.
2) Optimization of growth cycles by improving use of time, labor and facilities.
3) Up-scaling growth systems and reduction of marginal costs.

Together, the present solution may increase precision in the fast-growing microalgae industry and may increase reproducibility and stability in production. Moreover, the present embodiments may improve versatility in growing specific algal types.

The present embodiments may provide improved early detection and identification of specific stress.

Thus to summarize, an initial stage involves detecting the entire 480-840 nm range at 20 nm jumps with radiation sources at 20 different wavelengths, again at 20 nm jumps, and the relevant combinations are shown in FIG. 7. Then the question is how much of this data can be ignored and still provide a reliable answer.

The present embodiments thus may allow for data reduction and reducing the amount of processing. The present embodiments also aim to reduce the number of radiation sources and the number of detectors, and provide a cost-effective and practically feasible method of continuous monitoring.

As shown in FIGS. 10A and 10B the example successfully detects stress using a single radiation source at 440 nm, and two detectors, one at 480 nm and one at 680 nm. The fluorescence data at 480 nm works as a baseline. The data at 680 nm changes under stress compared to the baseline and thus gives them a solid indication of stress within four hours.

Figure 11:
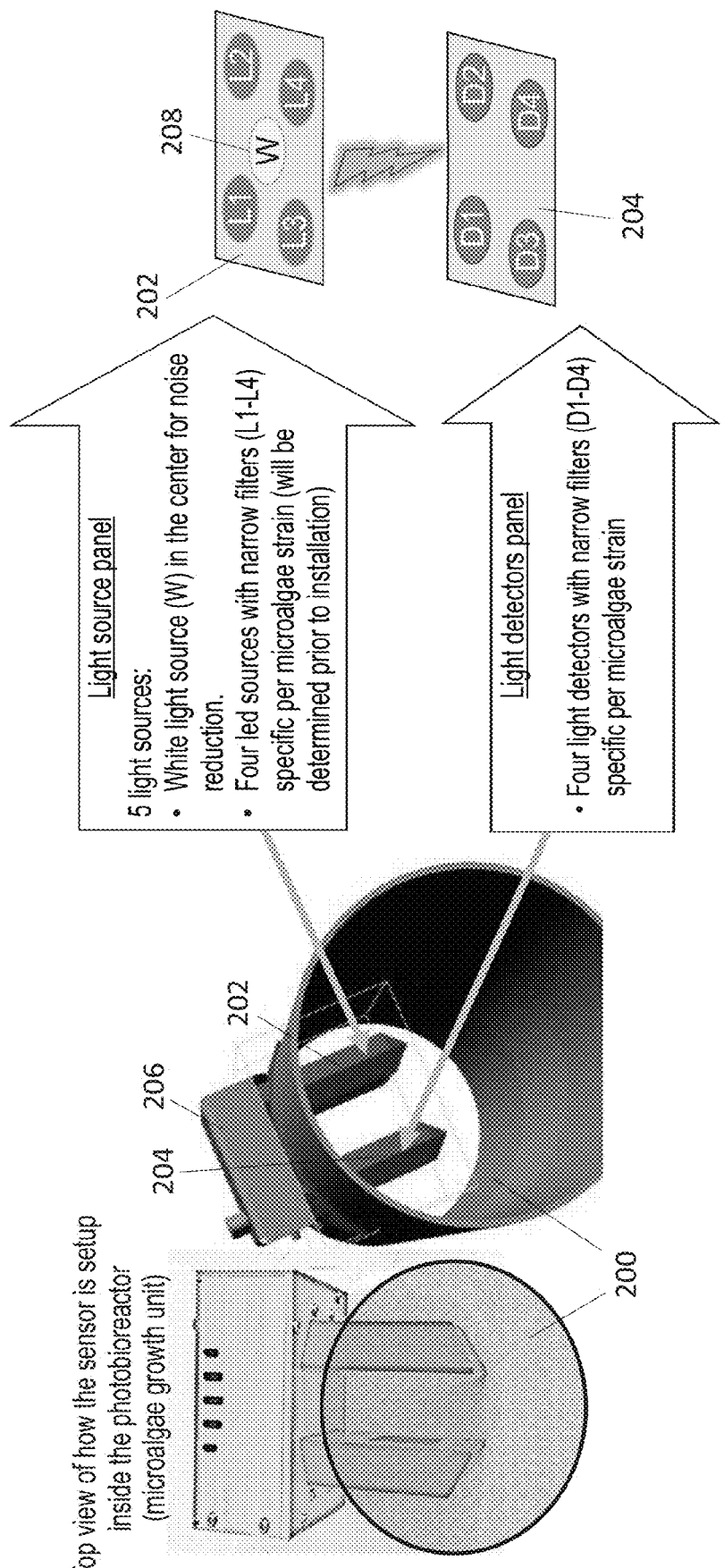
FIG. 11 is a diagram showing how the light source and sensor may be set up within a bioreactor according to embodiments of the present invention.

Reference is now made to FIG. 11, which illustrates a bioreactor 200 with sensors inserted. The sensors are arranged as two panels, a source panel 202 and a detection panel 204. The two panels extend from circuit box 206. In the source panel, 202, a central white light source 208 is surrounded by four LED sources with narrow filters, L1 . . . L4. The precise wavelengths of each of filters L1 . . . L4 are specific for each algal strain.

The detection panel 204 has four detectors D1 . . . D4, each specific to one of the four LED sources L1 . . . L4. The sources shine on the algae and the detectors detect the wavelengths resulting after absorption as explained above.

Reference is now made to FIGS. 12A-12F, which show stress responses for *P. Tricornutum*. FIG. 12A shows the effects of heat stress. Specifically, the *Tricornutum* growth curve under heat stress (28° C.)—right hand bars—is compared to a control (24° C.)—left hand bars. Cells were counted using a flow cytometer to give at least 5000 cells per count. Error bars represent ±one standard deviation.

FIG. 12B shows the effects of hyper salinity.

FIGS. 12C and 12D show nitrogen starvation. FIG. 12C shows the *P. Tricornutum* growth curve under nitrogen starvation (only 20% nitrogen amount)—right hand bars—compared to a control—left hand bars. Cells were counted using a flow cytometer giving at least 5000 cells per count.

FIG. 12D shows the *P. Tricornutum* chlorophyll fluorescence response to nitrogen starvation (only 20% nitrogen amount)—right hand bars—compared to a control. Chlorophyll fluorescence was measured using a flow cytometer (ex: 488 nm em: 700 nm) giving at least 5000 cells per count.

FIGS. 12E and 12F show metal starvation. FIG. 12E shows the *P. Tricornutum* growth curve under metal starvation (only 20% amount of metal)—right hand bars—compare to a control—left hand bars. Cells were counted using a flow cytometer giving at least 5000 cells per count. FIG. 12F shows the *P. Tricornutum* forward scatter (reflect cell size) response to metal starvation (only 20% metal)—right hand bars—compared to a control—left hand bars. Fluorescence was measured using a flow cytometer (ex: 488 nm) giving at least 5000 cells per count.

Figure 13A:
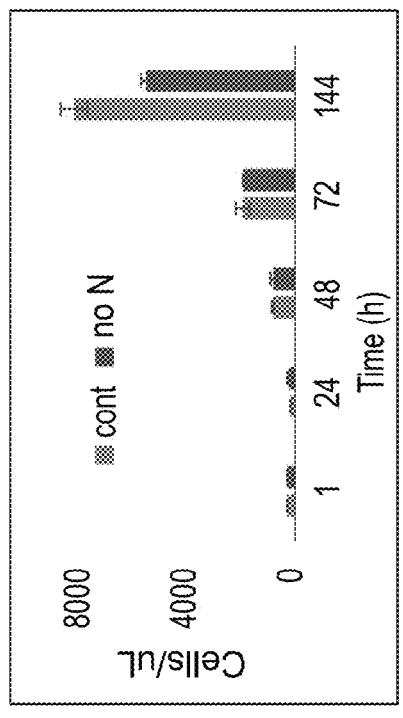
FIGS. 13A-13C illustrate hyper salinity, nitrogen starvation and metal starvation tests respectively on *N. Salina*.
Figure 13B:
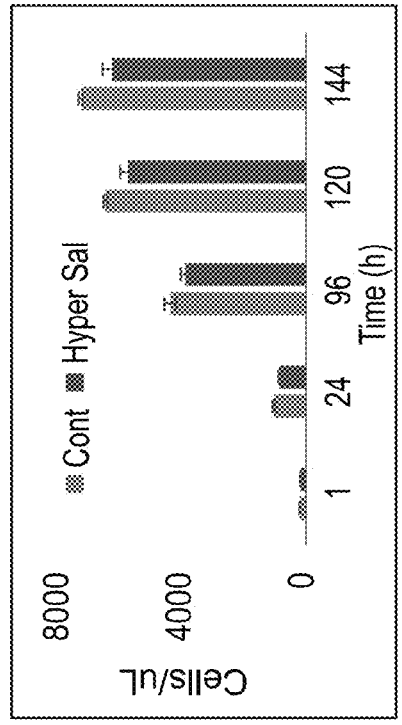
Figure 13D:
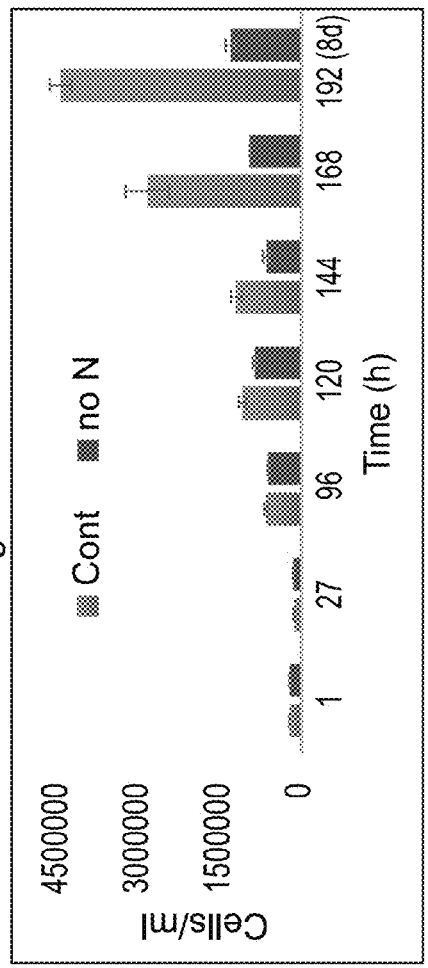
FIG. 13D illustrates a nitrogen starvation test on *C. desicatta*, according to the present embodiments.
Figure 13C:
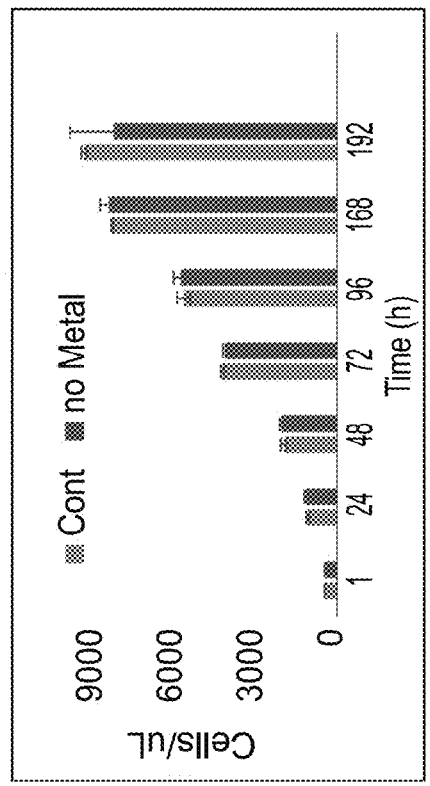

FIGS. 13A-13C illustrate hyper salinity, nitrogen starvation and metal starvation tests respectively on *N. Salina*. FIG. 13D illustrates a nitrogen starvation test on *C. desicatta*.

Reference is now made to FIGS. 14A and 14B, which show binary classifications of the algae into stressed and non-stressed populations 4 hours and 24 hours post stress initiation respectively. FIG. 14A shows a binary classification (*P. tricornutum*) based on all absorbance data 4 hours post stresses initiation, and FIG. 14B shows binary classification (*P. tricornutum*) based on all absorbance data 24 hours post stresses initiation. FIG. 14C shows a specific stress identification.

Reference is now made to FIGS. 15A-15F, which again show absorbance and all data classification. FIGS. 15A and 15B relate to a specific stress classification six hours after stress initiation. FIG. 15B shows the relative contribution of specific wavelengths in nm for the specific stress classification based on absorbance. FIGS. 15C and 15D relate to a specific stress classification eight hours after stress initiation. FIG. 15D shows the relative contribution of specific wavelengths in nm for the specific stress classification based on absorbance. FIGS. 15E and 15F relate to a specific stress classification twenty four hours after stress initiation. FIG. 15F shows the relative contribution of specific wavelengths in nm for the specific stress classification based on absorbance.

FIGS. 16A-C illustrate specific stress classifications for *P. tricornutum* based on absorbance in only 10 wavelengths, specifically the wavelengths 345 nm, 855 nm, 660 nm, 375 nm, 960 nm, 870 nm, 300 nm, 315 nm, 435 nm, 675 nm. FIG. 16A shows six hours post stress initiation. FIG. 16B shows eight hours post initiation and FIG. 16C shows classification based on absorption in ten wavelengths twenty four hours post initiation.

FIGS. 17A and 17B show specific stress classifications for *P. tricornutum* based on absorption in only five wavelengths, at six hours and eight hours post stress respectively.

In the present description, the terms "comprises", "comprising", "includes", "including", "having" and their conjugates mean "including but not limited to".

The term "consisting of" means "including and limited to".

As used herein, the singular form "a", "an" and "the" include plural references unless the context clearly dictates otherwise.

It is appreciated that certain features of the invention, which are, for clarity, described in the context of separate embodiments, may also be provided in combination in a single embodiment, and the present text is to be construed as if such an embodiment is specifically set forth. Conversely, various features of the invention, which are, for brevity, described in the context of a single embodiment, may also be provided separately or in any suitable subcombination or as suitable in any other described embodiment of the invention, and the present text is to be construed as if such separate embodiments and subcombinations are explicitly set forth. Certain features described in the context of various embodiments are not to be considered essential features of those embodiments, unless the embodiment is inoperative without those elements.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims.

It is the intent of the applicant(s) that all publications, patents and patent applications referred to in this specification are to be incorporated in their entirety by reference into the specification, as if each individual publication, patent or patent application was specifically and individually noted when referenced that it is to be incorporated herein by reference. In addition, citation or identification of any reference in this application shall not be construed as an admission that such reference is available as prior art to the present invention. To the extent that section headings are used, they should not be construed as necessarily limiting. In addition, any priority document(s) of this application is/are hereby incorporated herein by reference in its/their entirety.

What is claimed is:

1. A method for monitoring species of algae for stress comprising:
   growing a test set of algae of a first species;
   applying a stress of a predetermined kind to some of said algae, remaining algae being unstressed;
   irradiating said algae at a predetermined first set of irradiation wavelengths; said first set comprising a plurality of wavelengths;
   monitoring said algae at a predetermined second set of fluorescence/absorbance wavelengths to detect fluorescence and/or absorbance of said stressed algae and fluorescence and/or absorbance of said unstressed algae, said second set comprising a plurality of wavelengths;
   comparing detected fluorescence and/or absorbance for each irradiation wavelength between said stressed algae and unstressed algae to find signs indicating said applied stress;
   generating a plurality of combinations of respective irradiation wavelengths and fluorescence/absorbance wavelengths, wherein some of said combinations indicate said applied stress better than others of said combinations;
   searching through said combinations of respective irradiation wavelengths and detected wavelengths to find a minimal set of irradiating and detected wavelengths that detects said applied stress to a required level of reliability; and
   using said minimal set, irradiating further sets of algae of said first species to detect stress of said predetermined kind.

2. The method of claim 1, wherein said first set of wavelengths and said second set of wavelengths are built into optical matrices G(t) of detections at respective wavelength combinations, respective matrices containing results for different times.

3. The method of claim 2, comprising constructing variance (V) images collected per stress at said different times and generating a normalized G (NG) matrix, a relative dispersion (εG) matrix, a global ranked matrix (RG) and a line-ranked matrix (LG).

4. The method of claim 3, wherein said searching through combinations is carried out by applying machine learning to said matrices.

5. The method of claim 4, wherein said machine learning comprises using a combination of random decision forests and support vector machines.

6. The method of claim 4, wherein said machine learning comprises using convolutional neural networks.

7. The method of claim 1, wherein said stress of a predetermined kind is nitrogen stress.

8. The method of claim 1, wherein said second set of wavelengths comprises a range including 480 and 840 nm.

9. The method of claim 1, wherein said first set of wavelengths comprises a range including 440 nm and 800 nm.

10. The method of claim 8, wherein said range is covered in jumps of 20 nm.

11. The method of claim 1, wherein said irradiation is carried out using pulses.

12. The method of claim 1, wherein said first species is from the *Chlorella* genus.

13. The method of claim 1, wherein said minimal set comprises less than five irradiating wavelengths and less than ten detection wavelengths.

14. The method of claim 1, wherein said minimal set comprises less than three irradiating wavelengths and less than six detection wavelengths.

15. The method of claim 1, wherein said minimal set comprises one irradiating wavelength and two detection wavelengths.

16. The method of claim 1, wherein said detecting stress using said minimal set comprises detecting a scatter in amplitudes in a first wavelength of said detection wavelengths compared to a second wavelength of said detection wavelengths.

17. A method of monitoring growth of algae for stress, comprising:
   irradiating said algae at successive time intervals with at least one irradiation wavelength;

measuring fluorescence and/or absorbance from said algae at at least two detection wavelengths at said successive time intervals, said at least two detection wavelengths being different from said at least one irradiation wavelength;

comparing amplitudes of said at least two detection wavelengths at said successive time intervals, and determining presence of stress.

18. The method of claim 17, comprising:

selecting a first stress factor for testing; and selecting a corresponding set of at least one irradiation wavelength and at least two detection wavelengths.

19. The method of claim 17, wherein said determining presence of stress comprises detecting a scatter in amplitudes in a first of said detection wavelengths compared to a second of said detection wavelengths.

20. Apparatus for monitoring algal growth for stress, comprising:

an irradiation source configured to irradiate growing algae using at least one irradiation wavelength and configured to carry out said irradiation at successive time intervals;

a detector configured to detect fluorescence and/or absorbance from said growing algae, the detector configured to detect amplitudes, following said irradiation, at a plurality of detection wavelengths, said plurality of detection wavelengths being different from said at least one irradiation wavelength;

a comparator, configured to compare said amplitudes of said plurality of wavelengths at said successive time intervals and to determine from said comparison whether said growing algae is subject to a given stress.

21. The apparatus of claim 20, wherein said at least one irradiation wavelength and said plurality of detection wavelengths are selected for said given stress.

22. The apparatus of claim 20, wherein said at least one irradiation wavelength and said plurality of detection wavelengths are selected according to a species of said growing algae.

23. Apparatus for monitoring algal growth for stress, comprising:

an irradiation source configured to irradiate growing algae using at least one irradiation wavelength, said irradiation source further configured to carry out said irradiation at predetermined intervals;

a detector configured to detect fluorescence and/or absorbance from said growing algae, the detector configured to detect amplitudes, following said irradiation, at a plurality of detection wavelengths, said plurality of detection wavelengths being different from said at least one irradiation wavelength; and a communication link configured to send detection results to a remotely located comparator, the remotely located comparator configured to compare said amplitudes of said plurality of wavelengths at said predetermined intervals and to determine from said comparison whether said growing algae is subject to a given stress.

24. Apparatus for remote monitoring algal growth for stress, comprising:

an input for obtaining detection results of a remotely located detector positioned to detect fluorescence and/or absorbance from growing algae, the detector configured to detect amplitudes, following irradiation at an irradiation wavelength, said detection being at a plurality of detection wavelengths, said plurality of detection wavelengths being different from said at least one irradiation wavelength, said irradiation carried out at predetermined intervals;

a comparator, connected to said input, and configured to compare said amplitudes of said plurality of wavelengths at said predetermined intervals and to determine from said comparison whether said growing algae is subject to a given stress.

* * * * *